US008246832B2

(12) United States Patent
Lomas et al.

(10) Patent No.: US 8,246,832 B2
(45) Date of Patent: Aug. 21, 2012

(54) FLUIDICS DEVICE

(75) Inventors: Lee O. Lomas, Pleasanton, CA (US);
Jian Ding, Dublin, CA (US); Egisto Boschetti, Croissy-sur-Seine (FR)

(73) Assignee: Bio-Rad Laboratories, Inc., Hercules, CA (US)

( * ) Notice: Subject to any disclaimer, the term of this patent is extended or adjusted under 35 U.S.C. 154(b) by 907 days.

(21) Appl. No.: 11/915,151

(22) PCT Filed: Jan. 19, 2006

(86) PCT No.: PCT/US2006/001687
§ 371 (c)(1),
(2), (4) Date: Aug. 4, 2008

(87) PCT Pub. No.: WO2006/127056
PCT Pub. Date: Nov. 30, 2006

(65) Prior Publication Data
US 2009/0179146 A1 Jul. 16, 2009

Related U.S. Application Data

(60) Provisional application No. 60/684,177, filed on May 25, 2005, provisional application No. 60/702,989, filed on Jul. 28, 2005.

(51) Int. Cl.
*B01D 63/00* (2006.01)
(52) U.S. Cl. ..... 210/638; 210/650; 210/656; 210/198.2; 210/321.72; 210/335; 210/483; 422/70; 422/503; 422/527; 436/161; 436/178
(58) Field of Classification Search ............... 210/198.2, 210/656, 321.72, 335, 483, 638, 650; 204/451, 204/454, 456, 457, 601, 604, 606; 422/70, 422/82.05, 89, 502–505, 507, 527; 436/161, 436/164, 171, 178, 180; 137/833
See application file for complete search history.

(56) References Cited

U.S. PATENT DOCUMENTS
2,622,735 A * 12/1952 Criner .......................... 209/728
(Continued)

FOREIGN PATENT DOCUMENTS
EP          1 424 559 A1      6/2004
(Continued)

OTHER PUBLICATIONS

Chicz, R., et al., "Microcapillary Liquid Chromatography/Tandem Mass Spectrometry Using Alkaline pH Mobile Phases and Positive Ion Detection." Rapid Commun. in Mass Spectrometry, 2003, vol. 17; pp. 909-916.

(Continued)

*Primary Examiner* — Joseph Drodge
(74) *Attorney, Agent, or Firm* — Morgan, Lewis & Bockius LLP

(57) ABSTRACT

The present invention contemplates various devices that are configured to separate a sample, which contains more than one unique species, into any desired number of sub-samples by passing the sample across a like number of separation media configured for a first separation protocol. Each of the sub-samples may be further separated by an additional separation protocol, thereby creating a plurality of mini-samples, each of which may be further separated and/or analyzed. The invention also contemplates using a simple method of using conduits to form a fluid path that passes through a plurality of separation media, each of which media is configured to isolate a particular sub-sample. After various sub-samples of the sample are isolated by the various separation media, the conduits may be removed, thereby enabling each of the isolated sub-samples to be further separated and/or analyzed independent of any other sub-sample.

34 Claims, 13 Drawing Sheets

U.S. PATENT DOCUMENTS

| | | | |
|---|---|---|---|
| 2,708,516 A * | 5/1955 | Matheson et al. | 209/139.1 |
| 3,433,362 A * | 3/1969 | Robinson | 210/512.1 |
| 4,243,507 A | 1/1981 | Martin et al. | |
| 4,362,612 A | 12/1982 | Bier | |
| 4,963,236 A | 10/1990 | Rodkey et al. | |
| 4,971,670 A | 11/1990 | Faupel et al. | |
| 5,087,338 A | 2/1992 | Perry et al. | |
| 5,173,164 A | 12/1992 | Egen et al. | |
| 5,393,430 A | 2/1995 | Girot et al. | |
| 5,445,732 A | 8/1995 | Girot et al. | |
| 5,470,463 A | 11/1995 | Girot et al. | |
| 5,834,272 A | 11/1998 | Righetti | |
| 6,042,709 A * | 3/2000 | Parce et al. | 204/453 |
| 6,048,498 A * | 4/2000 | Kennedy | 422/503 |
| 6,309,608 B1 * | 10/2001 | Zhou et al. | 506/40 |
| 6,491,873 B2 | 12/2002 | Roberts et al. | |
| 6,585,939 B1 * | 7/2003 | Dapprich | 422/503 |
| 6,613,234 B2 | 9/2003 | Voute et al. | |
| 6,752,922 B2 * | 6/2004 | Huang et al. | 210/198.2 |
| 6,806,543 B2 * | 10/2004 | Yamakawa et al. | 257/414 |
| 6,827,095 B2 | 12/2004 | O'Connor | |
| 7,011,793 B2 * | 3/2006 | Zhou et al. | 422/503 |
| 7,279,134 B2 * | 10/2007 | Chan et al. | 422/503 |
| 2002/0182118 A1 | 12/2002 | Perry | |
| 2002/0187074 A1 * | 12/2002 | O'Connor et al. | 422/82.05 |
| 2003/0012697 A1 | 1/2003 | Hahn | |
| 2004/0219072 A1 * | 11/2004 | Yamakawa et al. | 422/100 |
| 2004/0226884 A1 * | 11/2004 | O'Connor et al. | 210/634 |
| 2005/0042149 A1 | 2/2005 | Bard | |
| 2007/0059218 A1 * | 3/2007 | Kane | 422/101 |

FOREIGN PATENT DOCUMENTS

| | | |
|---|---|---|
| WO | WO 2003/036304 | 5/2003 |
| WO | WO 2004022233 A1 | 3/2004 |
| WO | WO 2004079363 A1 | 9/2004 |
| WO | WO 2005/073711 | 8/2005 |
| WO | WO 2005/089911 | 9/2005 |

OTHER PUBLICATIONS

Dreger, M., et al., "Subcellular Proteomics." Mass Spectrometry Reviews, 2003, vol. 22; pp. 27-56.

Gerner, C., et al., "Concomitant Determination of Absolute Values of Cellular Protein Amounts, Synthesis Rates, and Turnover Rates by Quantitative Proteome Profiling." Mol. & Cellular Proteomics, 2002, vol. 528-537.

Hochstrasser, D.F., et al., "The Dynamic Range of Protein Expression: A Challenge for Proteomic Research." Electrophoresis, 2000, vol. 21; pp. 1104-1115.

Hunt, D. F., et al., "Phosphoproteome Analysis by Mass Spectrometry and Its Application to *Saccharomyces cerevisiae*." Nat. Biotechnology, 2002, vol. 20; pp. 301-305.

Lopez, M.F., "Better Approaches to Finding the Needle in Haystack: Optimizing Proteome Analysis through Automation." Electrophoresis, 2000, vol. 21; pp. 1082-1093.

Lopez, M.F., "High-throughput Profiling of the Mitochondrial Proteome Using Affinity Fractionation and Automation." Electrophoresis, 2000, vol. 21; pp. 3427-3440.

McDonald, T.G., et al.; "Mitochondrial Proteomics Undercover in the Lipid Bilayer." Basic Res. Cardiol., 2003, vol. 98; pp. 219-227.

Opiteck, G. J., et al., "Comprehensive Two-Dimensional High Performance Liquid Chromatography for Isolation of Overexpressed Proteins and Proteome Mapping." Anal Biochem., 1998, vol. 258; 349-361.

Patton, W. F., et al., "A Novel Subfractionation Approach for Mitochondrial Proteins: A Three-dimensional mitochondrial Proteome Map." Electrophoresis, 2001, vol. 22; pgs. 950-959.

Patton, W. F., et al., "Proteome Analysis II. Protein Subcellular Redistribution: Linking Physiology to Genomics via the Proteome and Separation Technologies Involved." J. Chromatography, 1999, vol. 722; pp. 203-223.

Regnier, F., et al., "Proteomics of Glycoprotein based on Affinity Selection of Glycopeptides from Trypic Digests." J. Chromatography, 2001 vol. 752; pp. 293-306.

Righetti, P.G., et al., "Preparative Electrophoresis with and without Immobilized pH Gradients." Advanced Electrophoresis, 1992, vol. 5; pp. 159-200.

Righetti, P.G., et al., "Preparative Protein Purification in Multi-Compartment Electrolyser with Immobiline Membranes." J. Chromatography, 1989, vol. 475; pp. 293-309.

Righetti, P.G., et al., "Preparative Purification of Human Monoclonal Antibody Isoforms in a Multi-Compartment Electrolyser with Immobiline Membranes." J. Chromatography, 1990, vol. 500; pp. 681-696.

Unger, K.K., et al., "An Automated On-Line Multidimensional HPLC System for Protein and Peptide Mapping with Integrated Sample Preparation." Anal. Chem., 2002, vol. 74, No. 4; pp. 809-820.

Wall, D., et al., "Isoelectric Focusing Nonporous RP HPLC: A Two-Dimensional Liquid-Phase Separation Method for Mapping of Cellular Proteins with Identification Using MALDITOF Mass Spectrometry." Anal. Chem., 2000, vol. 72, No. 6; pp. 1099-1111.

Yates, J. R. III, et al., "Direct Analysis of Protein Complexes Using Mass Spectrometry." Nature Biotech., 1999, vol. 17; pp. 676-682.

\* cited by examiner

(Row RZ)

(Row R1)

Single Buffer Flow

Absorbent Transition (eg pI 3, 4, 6, 8, 9)

Load Sample, Single Buffer Separate Proteins

Rotate Valves In Microfluidics System To Generate A New Flow Path

Elute Sub-samples From Ionic Characteristic Adsorbents And Load Onto Hydrophobic Characteristic Adsorbents C2 Resin
C4 Resin
C8 Resin
C18 Resin Adsorbent Transition (eg Hydrophobic Index)

Rotate Valves In Microfluidics System Of Hydrophobic Series To Generate A New Flow Path C2 Resin
C4 Resin
C8 Resin
C18 Resin

FLUIDICS DEVICE

CROSS-REFERENCES TO RELATED APPLICATIONS

The present application is a U.S. National Phase of PCT Patent Application No. PCT/US2006/001687 filed Jan. 19, 2006, and claims priority to U.S. Provisional Patent Application No. 60/684,177 filed May 25, 2005 and U.S. Provisional Patent Application No. 60/702,989 filed Jul. 28, 2005, each of which is incorporated herein by reference in its entirety for all purposes.

This application claims the benefit of the priority date of U.S. Provisional Application Ser. Nos. 60/684,177 filed on May 25, 2005 ("Fluidics Device," Boschetti et al.) and 60/702,989, filed Jul. 28, 2005 ("Separation Of Proteins Based On Isoelectric Point Using Solid-Phase Buffers," Boschetti et al.).

BACKGROUND

Current materials and methods for isolating the species in a given biological sample simply are not sufficient to isolate reliably all of the components of such a mixture. Typically, the dominant molecular species will mask those species present in concentrations less than about one one thousandth of the dominant species. For biological samples, such as blood, two of the most predominant molecular species are albumin and immunoglobulins. Attempts to identify various enzymes, antibodies, proteins, or secondary metabolites that may have relevance as disease markers, or which may be relevant for drug discovery, are complicated by the overall high abundance of albumin and immunoglobulins. As a result, the conventional resolving power, sensitivity, and loading capacity of the two most commonly used analytical techniques (i.e., 2-dimensional electrophoresis (2DE) and mass spectrometry) are limited. For example, the presence of such highly abundant proteins in a sample produces large signals with consequent signal overlap (in 2DE) or signal suppression (in mass spectrometry) of the other species present in the sample, which complicates analysis and undermines any conclusions about the catalog of molecular species present in the sample.

To isolate particular molecules, various separation protocols have been developed. For example, in gel electrophoresis proteins are uniformly coated with a negatively-charged detergent (e.g. SDS) and placed in the middleon one end (origin) of a buffered gel (e.g., polyacrylamide gel) between oppositely charged electrodes. When the electrodes are charged, each of the protein molecules travels toward one of the electrodes, according to their net charge at the pH of the buffered polyacrylamide gel the oppositely charged electrode. The speed, or mobility, at which the protein molecules move through the gel toward the electrodes is largely dependent on the size of the molecule, i.e., smaller molecules move faster through the gel matrix. As a result in the differences in mobility, types of protein molecules can be separated and then isolated based on their size.

A variant to gel electrophoresis is isoelectric focusing, which exploits the fact that the net charge of a protein depends on the environmental pH. Most generally, at acidic pH, proteins are globally positively charged while in alkaline pH they are negatively charged. The pH at which a protein has no net charge is called its isoelectric point ("pI"). Isoelectric focusing is an electrophoresis technique in which proteins move under an electric field through a pH gradient. All proteins migrate towards the cathode or the anode until they encounter a pH identical to their isoelectric point. At this isoelectric point the protein loses its charge and stops moving.

Proteins of different isoelectric points stop at different levels positions and are thus separated for subsequent identification. Accordingly, similarly sized molecules, which may move at similar speeds, can be separated after coming to rest at different pH points, as a result of having different pI values. In addition, there are situations in which migration by the size in a given buffered gel and migration by the isoelectric point are crossed for an enhanced separation of protein species from very complex mixtures; the technique used in this situation is called bidimensional electrophoresis. Unfortunately, migration of proteins within an electrophoresis gel network according to these techniques is a very slow process and is generally unacceptable for preparative purposes.

In response, various additional protocols have been developed which have attempted to increase the rate of separation, while preserving the accuracy by which it is performed. There are many types of devices comprising two or more subcompartments that are separated from each other by septa, e.g., monofilament screens, membranes, gels, filters, fritted discs, and the like (collectively, "membranes"). Generally, these devices are assembled from a plurality of essentially parallel frames or spacers, separated from each other by one or more membranes.

Multi-compartment electrolizerselectrolyzers with isoelectric membranes were introduced for processing large volumes and amounts of proteins to homogeneity. For example, see P. G. Righetti, et al., "Preparative Protein Purification in a Multi-Compartment Electrolyser with Immobiline Membranes," 475 J. CHROMATOGRAPHY 293-309 (1989); P. G. Righetti, et al., "Preparative Purification of Human Monoclonal Antibody Isoforms in a Multi-Compartment Electrolyser with Immobiline Membranes," 500 J. CHROMATOGRAPHY 681-696 (1990); P. G. Righetti, et al., "Preparative Electrophoresis with and without Immobilized pH Gradients," ADVANCES IN ELECTROPHORESIS 159-200 (1992). Based on isoelectric focus, this purification concept progresses under recycling conditions. The protein macro-ions are kept in a reservoir and are continuously passed through an electric field across a multicompartment electrolyzer equipped with zwitterionic membranes.

In this system the protein is always kept in a liquid vein, also called a "channel." Consequently, the protein is not lost by adsorption onto surfaces, as typically occurs in chromatographic procedures. Rather, the protein is trapped in a chamber that is delimited by two membranes that have pI values encompassing the pI value of the protein to be separated. Thus, by a continuous titration process, all other impurities, either non-isoelectric or having different pI values, are forced to leave the chamber. In the end, the isoelectric/isoionic protein of interest will ultimately be present, as the sole species, in the chamber. It should be recognized, however, that the isoelectric and isoionic points of a protein can differ to some extent in the presence of counterions.

U.S. Pat. No. 4,971,670 describes this process. Isoelectric membranes also are addressed in U.S. Pat. No. 4,243,507. U.S. Pat. No. 5,834,272 describes an immobilization of enzymes that keeps them in solution and, hence, under conditions of homogeneous catalysis. In U.S. Pat. No. 4,362,612, adjoining compartments are functionally designed to adjust to different pH values electrophoretically, thereby separating dissolved proteins according to their isoelectric points. Similar multiple subcompartments devices are described in U.S. Pat. Nos. 4,971,670, 5,173,164, 4,963,236, and 5,087,338. Each of these patents discloses a device, which is comprised of a series of parallel spacers, that are separated from each other by membranes, that provides an essentially parallel array of subcompartments.

Similarly, Amersham Pharmacia markets an IsoPrime filter using a plurality of pI-selective membranes arranged in series. In this device the membranes are arranged in ascending or descending pI-selectivity. As a solution passes through the membranes, molecules having pI values between two consecutive membranes are trapped between the membranes. However, this process takes on the order of hours to complete. Invitrogen, Inc. markets a device, the ZOOM IEF Fractionator, which is substantially similar to the IsoPrime device, but which enables the membranes to be individually replaced. However, like the IsoPrime, the ZOOM IEF Fractionator process takes on the order of hours to complete.

Various other separation protocols include: sub-cellular fractionation (Lopez, M. F., Electrophoresis, 2000, 21:1082-1093; Hochstrasser, D. F., et al., Electrophoresis, 2000, 21:1104-1115; Dreger, M., Mass Spectrometry Reviews, 2003, 22:27-56; Patton, W. F., J. Chromatography B, 1999, 722:203-223; McDonald T. G. et al., Basic Res. Cardiol., 2003, 98:219-227; Patton, W. F., et al., Electrophoresis, 2001, 22:950-959; Gerner C., et al., Mol. & Cellular Proteomics, 2002, 7:528-537), molecular sizing (Issaq, J. H., et al. 2003, Hochstrasser, et al. 2000), ion exchange (Lopez, M. F., 2000, 17), immobilized metal interaction chromatography ("IMAC") for calcium binding protein (Lopez, M. F., et al., Electrophoresis, 2000, 21:3427-3440) or phospho-proteins (Hunt, D. F., et al., Nat. Biotechnol., 2002, 20:301-305), hydrophobic (Lopez, 2000), heparine (Hochstrasser, et al. 2000) or lectin (Hochstrasser, et al. 2000, Lopez, 2000; Regnier, F., et al., J. Chromatography B, 2001, 752:293-306) affinity chromatography, and liquid chromatography (Issaq, J. H., et al 2002, Hochstrasser, et al. 2000).

Two-dimensional liquid chromatography used for intact protein fractionation, or their tryptic digests, generally uses reverse phase ("RP") for the second dimension, combined with ion exchange (Yates, J. R., Nature Biotech., 1999, 17:676-682, Unger, K. K., et al., Anal. Chem., 2002, 74:809-820), chromato-focusing (Wall, D., et al., Anal. Chem., 2000, 72:1099-1111), size exclusion (Opiteck, G., Anal. Biochem., 1998, 258:349-361), affinity (Regnier 2001), or another RP (Chicz R., et al., Rapid Commun. in Mass Spectrometry, 2003, 17:909-916) as the first chromatography step.

Unfortunately, multidimensional chromatography in proteomic fractionation generally never exceeds two dimensions due to high number of fractions to manage (pH-adjustment, desalting, re-injection in second dimension) and analyze, especially when a tedious analytical methods method such as 2DE makes the final bottleneck. In addition, a related shortcoming of the prior art is a relative inability to adapt the various devices to a particular separation protocol. For example, if a technician desires to identify 20 different proteins within a sample, a system involving only, e.g., eight separation media may be insufficient. In other words, if a sample contains 20 different proteins that have pI values that incrementally vary by 0.1 pH unit, a device having only eight separation media will fail to separate the proteins sufficiently. As a result, the proteins captured by each of the separation media (e.g., based on pI value) may need to be separated by way of a second separation protocol using the same type of separation (e.g., based on pI value).

What is needed, therefore, is an apparatus and a methodology and an apparatus that address at least one if not more of the deficiencies that afflict conventional practice, as previously described. More particularly, the need exists for an approach for separating molecules, such as proteins, quickly and accurately.

SUMMARY

An embodiment of the present invention addresses a device that includes, among other possible things, at least three chambers arrayed in a plate. The device has a first face on one side of the plate and a second face on a second, opposite side of the plate. Each chamber, independent of any other chamber, has an inlet opening to one face and an outlet opening to the other face. A plurality of the chambers are successively connected in series through removable conduits; each conduit connects an outlet of one chamber with an inlet of another chamber. The series of chambers and conduits defines a fluid path connecting an inlet of a first chamber through each of any intermediate chambers to an outlet of a last chamber.

In a further embodiment of this device, at least some of the conduits may pass through the plate and connect outlets opening to the second face with inlets opening to the first face. Additionally, in a further embodiment, all of the conduits may connect outlets opening to the second face with inlets opening to the first face.

In another further embodiment of this device, a plurality of the chambers in the series may be arrayed in a linear series (e.g., a row or a column). Each of the chambers may be adjacent a channel that opens to both faces. The fluid path between at least one outlet and inlet may pass through the channels.

In another further embodiment of this device, at least some of the conduits may connect outlets opening to the first face with inlets opening to the first face, or outlets opening to the second face with inlets opening to the second face. Additionally, in a further embodiment, at least one of the conduits may connect an outlet opening to the second face with an inlet opening to the second face. At least one of the conduits may connect an outlet opening to the first face with an inlet opening to the first face.

In another further embodiment of this device, the conduits may be removable from the device.

In another further embodiment of this device, at least one chamber in the series may contain a separation medium. Additionally, in a further embodiment, each of the chambers in the series may contain a separation medium. Moreover, a plurality of the chambers in the series may contain different separation media.

In another further embodiment of this device, the series of separation media may include, in the direction of the fluid path, either: (a) a high selective medium, a medium selective medium, and a low selective medium; or (b) a low selective medium, a medium selective medium, and a high selective medium.

In another further embodiment of this device, the plurality of chambers in the device may be a multiple of 8.

In another further embodiment of this device, the plurality of chambers in the device may be a multiple of 12.

In another further embodiment of this device, the chambers may be arrayed in at least one liner series.

In another further embodiment of this device, the chambers may be arrayed in a plurality of rows and columns. Additionally, in a further embodiment, the chambers may be arrayed in an eight-by-twelve array.

In another further embodiment of this device, the device may further include a plurality of series of chambers and conduits defining fluid paths.

In another further embodiment of this device, the device may further include a collection plate that includes a plurality of wells that are arranged, in rows and columns, to correspond to the chambers of the device. Each of the wells of the collection plate may have an inlet. Upon disengagement of the conduits, the inlets of the wells of the collection plate may be configured to align with the chambers of the device.

In another further embodiment of this device, the device may include a pump that is configured to push or pull a fluid sample along the fluid path.

In another further embodiment of this device, the device may further include a drip-through microtiter plate that includes wells corresponding to the chambers.

Another embodiment of the invention addresses a device that includes, among other possible things: (a) a plate including, among other possible things, at least one row of chambers, each chamber including, among other possible things, an inlet on a first face of the plate and an outlet on a second, opposite face of the plate; (b) a removable first member that sealingly engages the first face of the plate, wherein the first member includes: (I) a plurality of openings aligned with the inlets of a set of odd-numbered wells, and (II) a plurality of open-ended conduits aligned with a set of even-numbered wells, wherein the conduits pass from the inlets to the outlets of the even-numbered wells; (c) a removable second member that sealingly engages the first member, wherein the second member includes: (I) an opening aligned with the inlet of a first chamber, thereby forming the inlet to the first chamber; and (II) a plurality of conduits, wherein each of the conduits connects an opening of the first member to a conduit of the first member; (d) a removable gasket that sealingly engages the second face of the plate, wherein the gasket includes a plurality of openings aligned with the outlets of the chambers; and (e) a removable third member that sealingly engages the gasket, wherein the third member includes a plurality of grooves aligned with the openings in the gasket that, together, form a plurality of conduits, each conduit connecting the outlet of an odd-numbered well to the outlet of an even-numbered well. The combination of chambers and conduits defines a fluid path that passes through odd-numbered wells from inlet-to-outlet and through even-numbered wells from outlet-to-inlet.

In a further embodiment of this device, each of the odd-numbered chambers may contain a separation medium.

Another embodiment of the invention addresses a device that includes, among other possible things: (a) a plate including, among other possible things, at least one row of chambers, each chamber including, among other possible things, a first opening on a first face of the plate and a second opening on a second, opposite face of the plate, wherein the openings define inlets and outlets for each of the chambers; (b) a removable first member that sealingly engages the first face of the plate, wherein the first member includes: (I) an inlet port aligned with the first opening, which is configured to serve as inlet, of a first of the chambers in the row, and (II) a plurality of conduits that successively connect pairs of the first openings of other chambers in the row; (c) a removable gasket that sealingly engages the second face of the plate, wherein the gasket includes a plurality of openings aligned with the second openings of the chambers; and (d) a removable third member that sealingly engages the gasket, wherein the third member includes a plurality of conduits that successively connect pairs of the second openings of other chambers in the row. The combination of wells and conduits defines a fluid path passing from inlet of the chamber to the outlet of the last chamber in the row.

In a further embodiment of this device, each of the odd-numbered wells may contain a separation medium.

Another embodiment of the invention addresses a device that includes, among other possible things: (a) a plate that includes, among other possible things, at least one pair of first and second rows of wells, each well including, among other possible things, an inlet on a first face of the plate and an outlet on a second, opposite face of the plate; (b) a removable first member that sealingly engages the first face of the plate, wherein the first member includes, among other possible things: (I) a plurality of openings aligned with the inlets of wells in a first row, thereby defining chambers, and (II) a plurality of open-ended channels aligned with wells in a second row, wherein the channels define conduits passing from the inlets to the outlets of the wells; (c) a removable second member that sealingly engages the first member, wherein the second member includes, among other possible things: (I) an opening aligned with an opening in the first member that is aligned with an inlet of a first well in a first row, thereby forming the inlet to the first chamber; and (II) a plurality of grooves aligned with the openings of the first member that, together, form a plurality of conduits, each conduit connecting an $n^{th}$ inlet of a well in a first row with an $n^{th}$ inlet of a well in a second row; (d) a removable gasket that sealingly engages the second face of the plate, wherein the gasket includes, among other possible things, a plurality of openings aligned with the outlets of the wells; and (e) a removable third member that sealingly engages the gasket, wherein the third member includes, among other possible things: (I) a plurality of grooves aligned with the openings in the gasket that, together, form a plurality of conduits, each conduit connecting an $n^{th}$ outlet of a well in a first row with an $n+1^{th}$ outlet of a well in a second row; and (II) an opening aligned with an outlet of a last chamber. The combination of wells and conduits defines a fluid path passing from inlet to outlet of the wells in a first row.

In a further embodiment of this device, the second removable member may include, among other possible things, a first sub-part and a second sub-part, wherein: (1) the first sub-part includes, among other possible things, an opening aligned with the opening in the first member, and (2) the second sub-part includes, among other possible things, an opening aligned with the opening in the first member and a plurality of openings that form the grooves when the first sub-part is pressed against the second sub-part. In addition, the third removable member may include, among other possible things, a third sub-part and a fourth sub-part, wherein: (1) the third sub-part includes, among other possible things, an opening aligned with the outlet of the last chamber, and (2) the fourth sub-part includes, among other possible things, an opening aligned with the outlet of the last chamber and a plurality of openings that form the grooves when the third sub-part is pressed against the fourth subpart.

In another further embodiment of this device, the odd-numbered wells may contain a separation medium.

Another embodiment of the invention addresses a method that includes, among other possible steps: (a) providing a device that includes, among other possible things, at least three chambers arrayed in a plate, wherein (i) the device has a first face on one side of the plate and a second face on a second, opposite side of the plate, (ii) each chamber, independent of any other chamber, has an inlet opening to one face and an outlet opening to the other face; (iii) a plurality of the chambers are successively connected in series through removable conduits, wherein each conduit connects an outlet of one chamber with an inlet of another chamber; (iv) the series of chambers and conduits defines a fluid path connecting an inlet of a first chamber through each of any intermediate chambers to an outlet of a last chamber; and (v) each chamber in the series includes a different separation medium; (b) flowing a sample including, among other possible things, a plurality of analytes along the fluid path from the inlet of a first chamber through the outlet of the last chamber, whereby the separation media capture analytes having affinity for the media; (c) removing the conduits that connect outlets to inlets from the device; (d) eluting captured analytes independently from the chambers; and (e) collecting the eluted analytes.

In a further embodiment of this method, the method may also include the step of detecting analytes eluted from at least one chamber. Additionally, in a further embodiment of this method, the step of detecting analytes may be performed by mass spectrometry or gel electrophoresis.

In a further embodiment of this method, the step of eluting may include eluting from at least one chamber in a plurality of fractions.

In a further embodiment of this method, the sample may be selected from the group consisting of blood, urine, cerebrospinal fluid and derivatives thereof.

In another further embodiment of this method, the method may further include the step of (b)(1) separating at least one of the analytes captured by the separation media into two or more mini-samples.

In another further embodiment of this method, the method may further include the step of (b)(1) separating at least one of the analytes captured by the separation media into two or more mini-samples using one or more of the following protocols: mass spectrometry, isoelectric focusing, hydrophobicity, and/or hydrophilicity.

Another embodiment of the invention addresses a kit. The kit includes, among other possible things: (a) a device that includes, among other possible things: at least three chambers arrayed in a plate, wherein (i) the device has a first face on one side of the plate and a second face on a second, opposite side of the plate, (ii) each chamber, independent of any other chamber, has an inlet opening to one face and an outlet opening to the other face; (iii) a plurality of the chambers are successively connected in series through removable conduits, wherein each conduit connects an outlet of one chamber with an inlet of another chamber; and (iv) the series of chambers and conduits defines a fluid path connecting an inlet of a first chamber through each of any intermediate chambers to an outlet of a last chamber; and (b) at least one container containing a separation medium.

Another embodiment of the present invention addresses a method for the multidimensional separation of analytes comprising: (a) separating analytes in a sample into a plurality of first aliquots by: (i) providing a first series of different first sorbents arranged sequentially and in fluid communication from first to last; (ii) flowing the sample through the first series from first to last so that the sample sequentially contacts the different sorbents, wherein the first sorbents capture analytes based on a first physical-chemical property and the sequence of first sorbents is ordered from first to last in decreasing selectivity with respect to the first physical-chemical property by which the sorbents bind analytes in the sample, whereby each of the sorbents captures a different set of analytes; and (iii) eluting analytes from a plurality of the sorbents into the plurality of first aliquots; (b) separating analytes in each of a plurality of the first aliquots into a plurality of second aliquots by independently: (i) providing a second series of different second sorbents arranged sequentially and in fluid communication from first to last; (ii) flowing a first aliquot through the second series from first to last so that the sample sequentially contacts the different sorbents, wherein the second sorbents capture analytes based on a second, different physical-chemical property and the sequence of second sorbents is ordered from first to last in decreasing selectivity with respect to the second physical-chemical property by which the sorbents bind analytes in the sample, whereby each of the sorbents captures a different set of analytes; and (iii) eluting analytes from each of the sorbents into the plurality of second aliquots; and (c) separating the analytes in a plurality of second aliquots by mass spectrometry.

In a further embodiment of this method, the first series of sorbents may bind analytes based on isoelectric point and may be ordered to capture analytes from highest to lowest isoelectric point or from lowest to highest isoelectric point.

In another further embodiment of this method, each of the first sorbents may include a solid buffer and an ion exchange material. Further, the second series of sorbents may bind analytes based on hydrophobic index and may be ordered to capture analytes from most hydrophobic to least hydrophobic. Further, each of the second sorbents may include a hydrocarbon chain and an amine ligand. Further, the hydrocarbon chain of each sorbent in the series may include more carbons than that of a previous sorbent.

In another further embodiment of this method, the first series of sorbents may bind analytes based on hydrophobic index and may be ordered to capture analytes from most hydrophobic to most least hydrophobic. Each of the first sorbents may include a hydrocarbon chain and an amine ligand. The hydrocarbon chain of each sorbent in the series may include more carbons than that of a previous sorbent. The second series of sorbents may bind analytes based on isoelectric point and may be ordered from highest to lowest isoelectric point or from lowest to highest isoelectric point. Each of the second sorbents may include a solid buffer and an ion exchange material.

In another further embodiment of this method, the mass spectrometry may be laser desorption/ionization mass spectrometry.

In another further embodiment of this method, the mass spectrometry may be electrospray mass spectrometry.

Another embodiment of the present invention addresses a device. This device includes, among other possible things: a plurality of intersecting row and columns arranged in a plate. Each of the rows includes a plurality of sample chambers that are configured to be fluidically connected to the other chambers in the row. Each of the columns includes a plurality of sample chambers that are configured to be fluidically connected to the other chambers in the row. At least some of the chambers in one of the rows include chromatographic separation media that are configured to capture molecules that have pI values within a given range; the chromatographic separation media of the chambers are sequentially arranged from lowest-to-highest or highest-to-lowest in the chambers in the row. At least some of the chambers in at least one of the columns include hydrophobic separation media that are configured to capture molecules that have hydrophobicity values within a given range; the hydrophobic separation media of the chambers are sequentially arranged from lowest-to-highest or highest-to-lowest in the chambers in the column.

Another embodiment of the present invention addresses a method for the multidimensional separation of analytes. This method includes, among other possible steps: (a) providing a device comprising a plurality of intersecting row and columns arranged in a plate, wherein each of the rows comprises a plurality of sample chambers that are configured to be fluidically connected to the other chambers in the row, wherein each of the columns comprises a plurality of sample chambers that are configured to be fluidically connected to the other chambers in the row, wherein at least some of the chambers in one of the rows comprise chromatographic separation media that are configured to capture molecules that have pI values within a given range and wherein the chromatographic separation media of the chambers are sequentially arranged from lowest-to-highest or highest-to-lowest in the chambers in the row, wherein at least some of the chambers in at least one of the columns comprise hydrophobic separation media that are configured to capture molecules that have hydrophobicity values within a given range and wherein the hydrophobic separation media of the chambers are sequentially arranged from lowest-to-highest or highest-to-lowest in the chambers in the column; (b) providing a sample to a first chamber in the row that comprises the chambers that contain the chromatographic separation media; (c) separating the sample into a plurality of sub-samples respectively provided in each of the chambers of the row by passing the sample through the series of chromatographic separation media in the row; and (d) separating the subsample in at least one of the chambers of the row into a plurality of minisamples respectively provided in each of the chambers of the intersecting column by passing the sample through the series of hydrophobic separation media in the column.

These and other features, aspects, and advantages of the present invention will become more apparent from the following description, appended claims, and accompanying exemplary embodiments shown in the drawings

DETAILED DESCRIPTION

Figure 1:
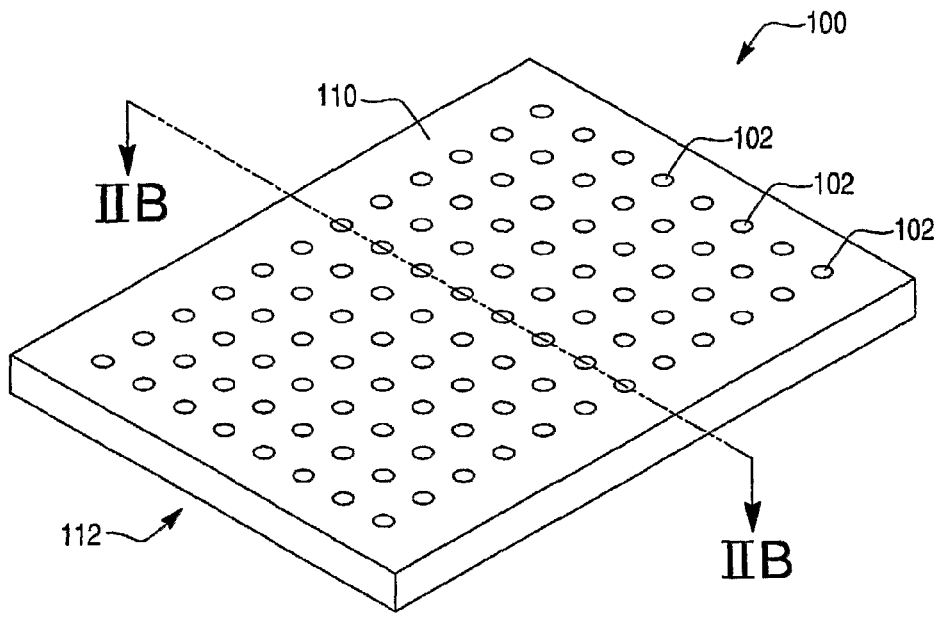
FIG. 1 is a perspective view of a microtiter plate that contains 96 chambers arranged in an eight by twelve matrix and that is used in a first embodiment of the present invention.

Presently preferred embodiments of the invention are illustrated in the drawings. An effort has been made to use the same reference numbers throughout the drawings to refer to the same or like parts.

This invention provides a fluidics device comprising a series of chambers arrayed in a plate and having inlets and outlets connected by removable conduits. The plate of this invention is, preferably, a microtiter plate such as drip plate or a filter plate. However, in other embodiments, the plate may comprise a piece comprising channels, such as bores, that open on either side of the piece and that will define chambers when conduits are attached to the openings of the bores. Preferably, the chambers are arrayed substantially in a plane.

The combination of chambers and conduits define a fluid path whereby a fluid can be pumped from chamber to chamber. Preferably, each chamber in the series comprises a different separation medium that can capture a different subset of analytes in a complex sample. A particular utility of this device is that the conduits are removable so that analytes captured by a separation medium in any chamber can be isolated by, e.g., eluting the analytes from the chambers. Once isolated, the analytes can be detected or analyzed by any available methodology.

Presently preferred embodiments of the invention are illustrated in the drawings. An effort has been made to use the same, or like, reference numbers throughout the drawings to refer to the same or like parts.

Each embodiment of the present invention, as hereafter described in detail, may use standard microtiter filtration plates arranged in, e.g., a typical 96-chamber (eight rows by twelve columns) format. Other formats also can be used, e.g., plates with any multiple of eight chambers, any multiple of twelve chambers, any multiple of 96 chambers (e.g., a 386 chamber plate), etc. Each chamber of the filtration plate may contain a particular type of separation media, e.g., chromatographic resins (e.g., packed-bed or fluidized-bed).

In a first embodiment (which will later be described with respect to FIGS. 1-4), the fluid is forced alternately down through one chamber in the series (e.g., a column or a row), up through the next chamber in series, down through the next chamber in the series, up through the next chamber in the series, and so on. More specifically, the bottom opening of a first chamber in a series (e.g., column or row) may be connected to the bottom opening of a second chamber in that series. The top opening of the second chamber may be connected to the top opening of a third chamber in that row (or column). The sequencing of connecting bottom-to-bottom and top-to-top generates a flow path that travels from top-to-bottom of the first chamber, then bottom-to-top of second chamber, and then top-to-bottom of third chamber, etc.

In a second embodiment (which will later be described with respect to FIGS. 5-7), the fluid is forced down through each chamber in the series. More specifically, the bottom opening of a first chamber in a column (or row) may be connected to the top opening of a second chamber in that column (or row). The bottom opening of the second chamber may be connected to the top opening of a third chamber in that row (or column). The sequencing of connecting bottom-to-top generates a flow path that travels from top-to-bottom of the first chamber, top-to-bottom of second chamber, top-to-bottom of third chamber, etc.

In other embodiments, these arrangements can be mixed, including both bottom-to-bottom/top-to-top and bottom-to-top connections.

With any of the aforementioned embodiments, a series of parallel separation protocols may simultaneously occur along each of the columns (or rows). In other words, different samples can be provided to the first chamber in given column (or row); each of the samples may then pass through each of the chambers (and the varying separation media therein) in its respective row. Each of the separation media through which a particular sample passes serves to capture a portion of the sample such that upon reaching the final chamber in the given row, various portions of the sample will be retained in each of the chambers through which the sample passed. Moreover, upon completion of the sample's separation, each of the sample portions (or "sub-samples") may be transferred to a collection plate for, if desired, further analysis (e.g., mass spectrometry, gel electrophoresis, etc.) or separation.

More specifically, each sample may be introduced to the device via the first chamber of a particular column (or row). The sample may then be pumped through the device via, e.g., a peristaltic pump (at a variety of suitable flow rates), until the sample passes through all separation media in each of the chambers in that column (or row). After the sample is bound across each of the separation media, all connecting tubes and/or conduits may be removed. As a result, the device may serve as a typical sample-filled filter plate operating in batch or continuous flow mode. However, each of the separation media may be, if desired, processed independently of any other separation media. Moreover, the sample can be removed from each of the chambers of the microtiter plate by, e.g., vacuum or centrifugation.

The first embodiment will now be described with respect to FIGS. 1-4. As shown in FIG. 1, a microtiter plate 100 includes a plurality of chambers 102 that are arranged in a matrix of rows and columns. Each of the chambers 102 is substantially in a plane that is defined by upper and lower faces 110, 112 of the microtiter plate 100. As shown, the microtiter plate 100 may include, e.g., 96 chambers arranged in an eight by twelve matrix. Neither the number of chambers 102 nor the number of rows/columns, however, is critical to the invention. Rather, any suitable number of chambers 102 can be used. Moreover, a technician may choose a microtiter plate based on the number of chambers therein and a corresponding number of chambers needed for a particular separation protocol.

Figure 2A:
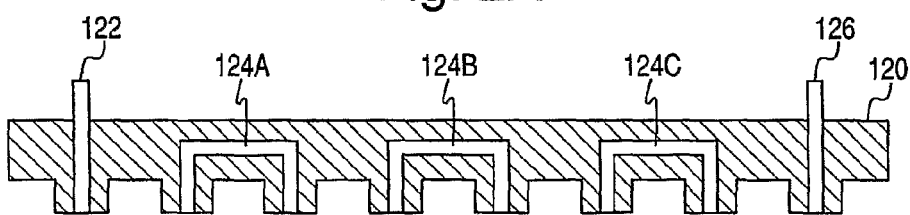
FIG. 2A is a cross-sectional view of an upper conduit plate according to a first embodiment of the present invention.
Figure 2B:
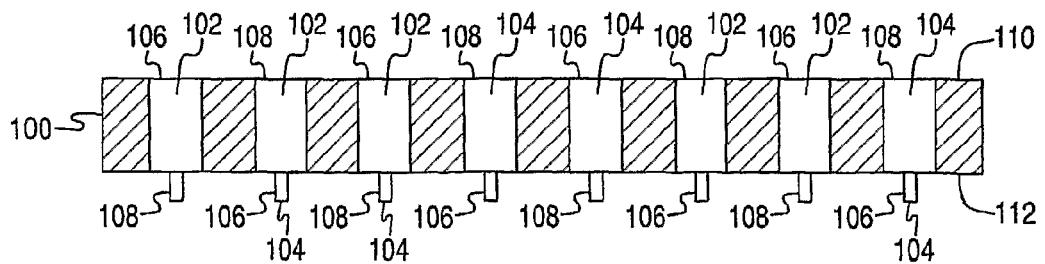
FIG. 2B is a cross-sectional view of the microtiter plate of FIG. 1 taken along lines IIB-IIB.

FIG. 2B shows a cross-section of the microtiter plate 100. As shown in FIG. 2B, each of the chambers 102 of the microtiter plate 100 has two openings 104, one of which serves as an inlet 106 and the other of which serves as an outlet 108. Whether an opening 104 of a particular chamber 102 serves as inlet 106 or as an outlet 108, however, will depend on the direction of flow through the chamber 102, as later described in detail. That is to say, whether a particular opening in a chamber is an inlet or an outlet is independent of the face on which the opening opens.

Positioned above and below the microtiter plate 100, are first and second conduit plates 120, 140, respectively. The first conduit plate 120 (shown in FIG. 2A) includes an inlet port 122 and an outlet port 126. Between the inlet and outlet ports 122, 126, is a series of conduits 124. As shown, for example, the first plate 120 may have three conduits 124A, 124B, 124C that correspond to a particular set (e.g., a row) of chambers 102 in the microtiter plate 100.

Similar to the first plate 120, the second plate 140 also contains a plurality of conduits 144. As shown, the second plate 140 may contain, e.g., four conduits 144A, 144B, 144C, 144D that correspond to a particular set (e.g., a row) of chambers 102 in the microtiter plate 100. In addition, although the shown embodiment of the second plate 140 does not include inlet and/or outlet ports, other embodiments of the invention (e.g., where a separation will involve an odd number of chambers) may include an outlet (or inlet) in the second plate 140.

Some versions of the embodiment may also include a gasket 160 that is configured to be positioned between the lower plate 140 and the microtiter plate 100. The gasket 160 may serve to seal the lower plate 140 to the microtiter plate 100.

When the first and second plates 120, 140 are connected (and possibly sealed by the gasket 160) to the upper and lower faces 110, 112, respectively of the microtiter plate 100, a fluid pathway (which is indicated by arrows in FIG. 3) is established. The fluid pathway extends between, e.g., a first chamber 102A in a row and a last chamber 102H in that row. More specifically, a sample can pass through the inlet port 122 in the first plate 120 and through the inlet 106A of a first chamber 102A. A sub-sample of the sample may be retained within the first chamber 102A by, e.g., a separation media (not shown) provided therein. The sample remainder, passes through the outlet 108A of the first chamber 102A, though a first conduit 144A in the second plate 140, and through the input 106B of a second chamber 102B. Subsequently, another sub-sample may be retained within the second chamber 102B by means of a different separation media (not shown) provided in the second chamber 102B. Similarly, that which remains of the original sample (after passing through the separation media in the first and second chambers 102A, 102B) passes through the output 108B of the second chamber 102B, through a conduit 124A in the first plate 120, and through the inlet 106C of a third chamber 102C in which another sub-sample may be retained.

This iterative process continues until that which remains of the sample passes through a separation media (not shown) in the last chamber 102H. At this point, depending on the embodiment, the remaining sample may be removed from the last chamber 102H by means of the outlet port 126 in the first plate 120. In other embodiments, however, the separation may continue into a different row (or column) by either: (a) providing another conduit 124 (not shown) in the first plate 120 that connects the outlet 108H of the last chamber 102H with the inlet 106 of a chamber 102 in the different row (or column); or (b) connecting the outlet port 126 in the first plate 120 to an inlet 106 of a chamber 102 in the different row (or column).

Regardless of the number of chambers 102 through which a sample passes, numerous means exist to aid the movement of the sample. For example, a pump (e.g., a peristaltic pump)

could be connected to the inlet port 122 of the first plate 120; this pump could push the sample through the chambers 102. Alternatively (or additionally), a pump (e.g., a peristaltic pump) could be connected to the outlet port 126 of the first plate 120; this pump could pull the sample through the chambers 102.

Other related devices of this embodiment contemplate compound (or "bidimensional") separation protocols. For example, if the first and second plates 120, 140 were used to separate a sample into eight sub-samples (e.g., in chambers 102A-102H) in a particular row, each of those sub-samples could be further separated along its respective column into a plurality (e.g., twelve) of mini-samples.

In one such embodiment, the first and second plates 120, 140 could be replaced with alternate plates (not shown) that contain conduits that connect chambers within a particular column of the plate. As a result, if the first separation protocol (using the first and second plates 120, 140) were along a particular row and were based on a first separation protocol, each of the remaining chambers in the various columns could be used for further separation based on a second separation protocol. In other words, each of the sub-samples could flow through separation media in the chambers of their respective columns. As a result, if, e.g., an eight by twelve matrix of chambers were employed, after a first separation protocol, eight sub-samples could be obtained. And, after a second separation protocol, 96 individual mini-samples could be obtained.

In addition to the foregoing compound separation, each of the mini-samples in, e.g., the chambers in a particular column could be transferred (by means later described in detail) to a like-sized column of another microtiter plate (not shown) where they could be further separated, by means of a third separation protocol, along the rows thereof. Alternatively or additionally, each of the individual mini-samples could be further analyzed and/or separated using any conventional other analytical or separation protocol (e.g., chromatography, isoelectric focusing, hydrophobicity, hydrophilicity, size exclusion, mass spectrometry, gel electrophoresis, ion exchange, various other separation protocols (some of which are later described as embodiments of the present invention), etc.), thereby adding another dimension to the separation of the original sample. Moreover, if, e.g., an additional chromatography separation protocol were to be employed, any conventional chromatography technique (e.g., ion exchanges, hydrophobic solid phases, affinity sorbents, metal chelating resins, gel filtration material, hydroxyapatite crystals, etc.) may be used.

Figure 4:
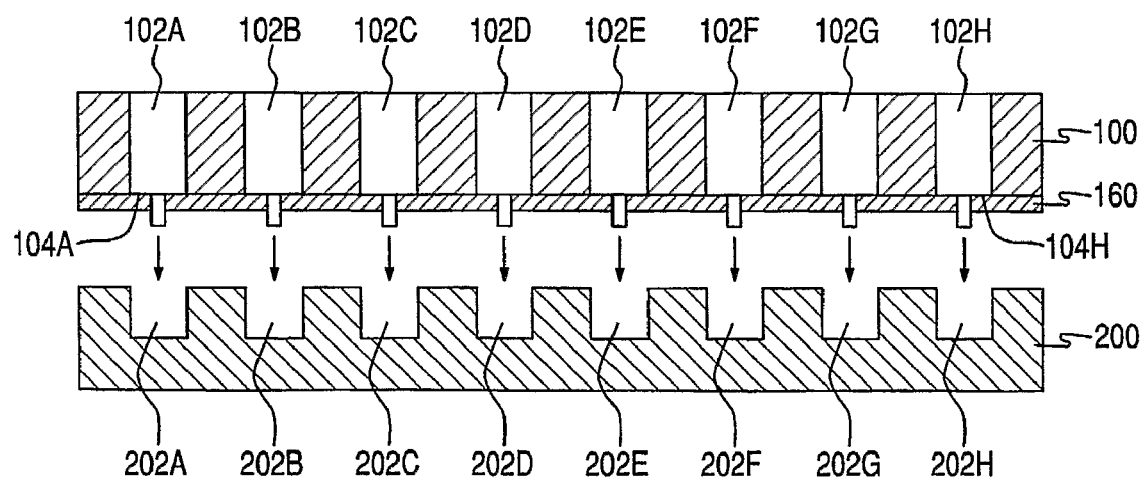
FIG. 4 is a cross-sectional view of the microtiter plate of FIGS. 1 and 3 aligned with a collection plate.

To move each of the mini-samples of, e.g., a row, a column, or a matrix to a more permanent storage device, a collection plate 200 of the type shown in FIG. 4 could be employed. In this embodiment, the second plate 140 (with or without the gasket 160) may be detached from the microtiter plate 100 and the openings 104 on the lower side of the microtiter plate 100 may be aligned with wells 202 in the collection plate 200. The sub-samples (or mini-samples after a compound separation) may pass into the wells 202 of the collection plate 200 by any conventional means, e.g., force of gravity, vacuum, etc.

Similarly, in other related embodiments, the top plate 120 may be removed to enable one or more solvents to be added to sub-samples/mini-samples (e.g., analytes) housed within the chambers 102 via the chambers' upper openings 104. Moreover, the solvent(s) could be used to facilitate draining the sub-samples/mini-samples through the chambers' lower openings 104 of the chambers 102 (i.e., the sub-samples/mini-samples could drip out of the chambers 102 and into, e.g., a collection plate 200).

Figure 5:
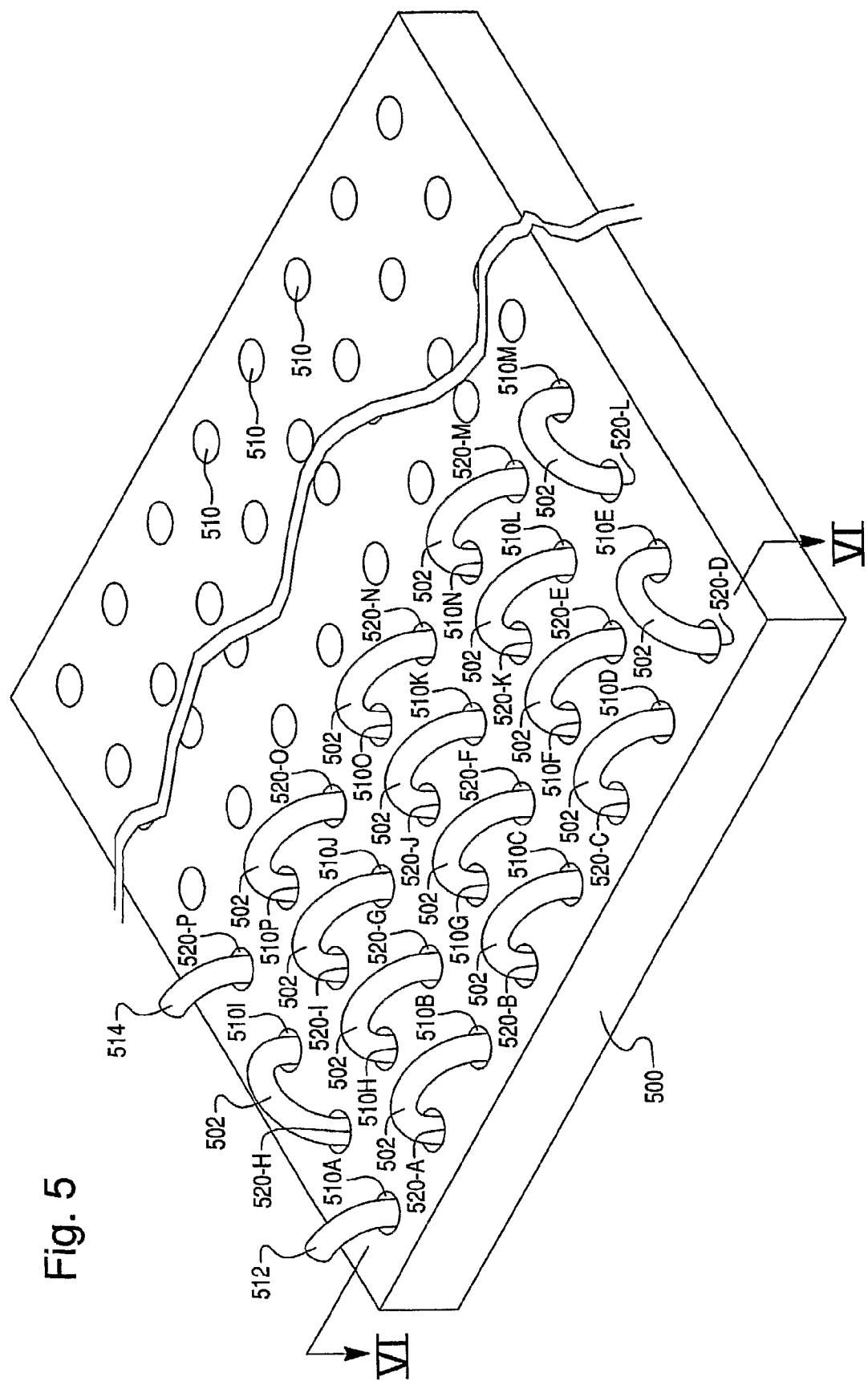
FIG. 5 is a perspective view of a microtiter plate that contains 96 chambers arranged in an eight by twelve matrix and that is used in a second embodiment of the present invention.
Figure 6:
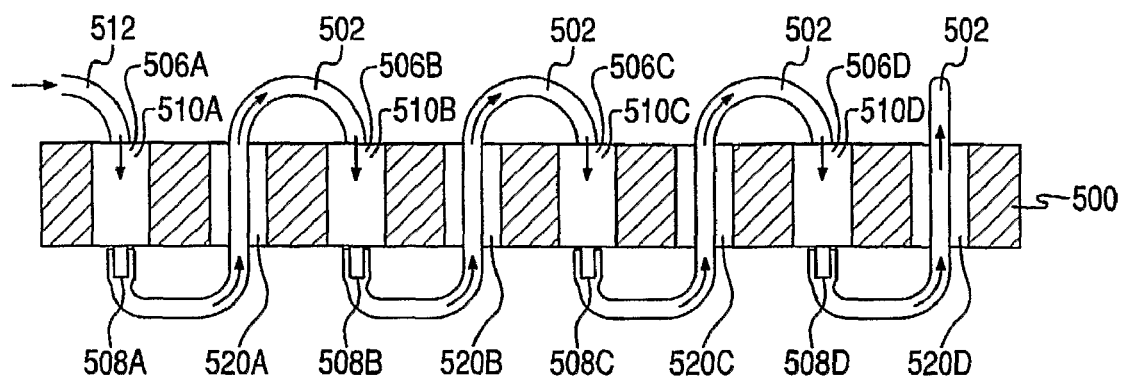
FIG. 6, which is a cross-sectional view of the microtiter plate of FIG. 5, shows a plurality of conduits that extend from outlets of certain chamber to inlets of other chambers.
Figure 7:
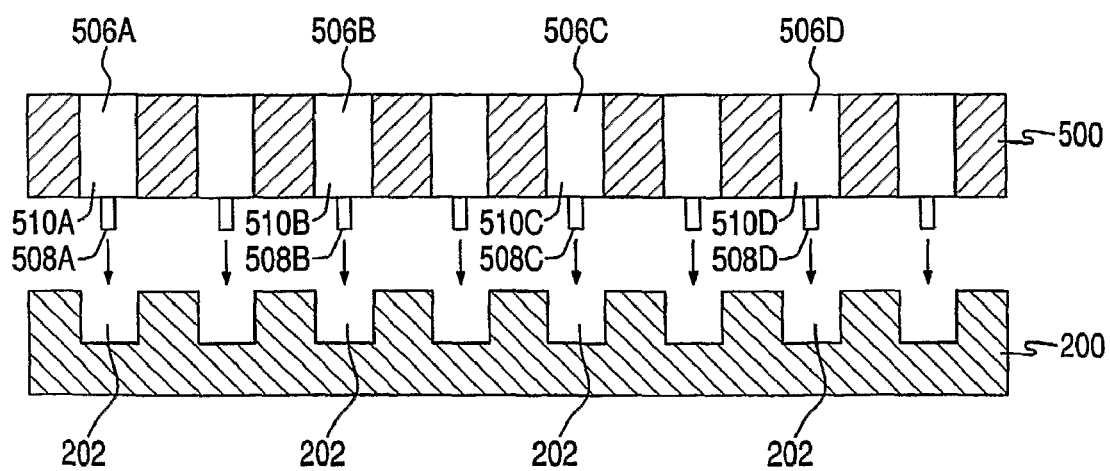
FIG. 7, which is a cross-sectional view of microtiter plate of FIG. 6 aligned with a collection plate, shows the conduits disconnected from the outlets of the chambers.

Another embodiment of the present invention will hereafter be discussed with respect to FIGS. 5-7. In this embodiment, separable conduits 502 connect outlets-to-inlets of various chambers 510 in, e.g., a standard eight by twelve microtiter plate 500. As shown in FIG. 5, one advantage of this embodiment is that a technician can readily connect as many chambers 510 as desired. More specifically, as shown, a technician could connect an inlet port 512 to an inlet 506 of a first chamber 510A. Subsequent conduits 502 may then connect, e.g. a total of sixteen chambers 510-A to 510-P in series. Finally, an outlet 508 of the last chamber 510-P in the series may be connected to an outlet port 514. Adjacent each of the chambers 510-A to 510-P in the linear series in which a separation is to occur, there is provided an access channel 520-A to 520-P, which may, in some embodiments, be another chamber that is not being used to conduct a separation protocol.

As shown in FIG. 6, the access channels 520-A to 520-P enable conduits 502 to pass through the microtiter plate 500, thereby serving to connect the outlet 508 of one chamber (e.g., 510A) on one (lower) side of the plate 500 with the inlet 506 of a second chamber (e.g., 510B) on a second (upper) side of the plate 500. As a result of this flexible structure, a technician may readily connect as many chambers 510 as desired. Moreover, when the chambers 510 are connected, a sample may flow top-to-bottom therethrough in manner that is generally in the shape of a square-wave.

Regardless of the number of chambers 510 through which a sample passes, numerous means exist to aid the movement of the sample. For example, a pump (e.g., a peristaltic pump) could be connected to the inlet port 512 of the first chamber 510A; this pump could push the sample through the chambers 510-A to 510-P. Alternatively (or additionally), a pump (e.g., a peristaltic pump) could be connected to the outlet port 514 of the last chamber 510-P; this pump could pull the sample through the chambers 510-A to 510-P.

Each of the sub-samples (or mini-samples for compound separations) may be transferred to a chamber in another microtiter plate where they may be more permanently stored, further analyzed (e.g., using mass spectrometry, gel electrophoresis, etc.), and/or separated (e.g., using hydrophobicity). To move each of the sub-samples (or mini-samples) to a more permanent storage device, a collection plate 200 of the type shown in FIG. 7 may be employed. In this embodiment, the conduits 502 may be detached from the outlets 508, which, in turn, may be aligned with wells 202 in the collection plate 200. The sub-samples (or mini-samples after a compound separation) may pass into the wells 202 of the collection plate 200 by any conventional means, e.g., force of gravity, vacuum, etc.

Similarly, in other related embodiments, the conduits 502 may be removed to enable one or more solvents to be added to sub-samples/mini-samples (e.g., analytes) housed within the chambers 510 via the chambers' inlets 506. Moreover, the solvent(s) could be used to facilitate draining the sub-samples/mini-samples through the chambers' outlets 508 (i.e., the sub-samples/mini-samples could drip out of the chambers 510 and into, e.g., a collection plate 200).

Similar to the aforementioned embodiment of FIGS. 1-4, when a technician has separated a sample into a plurality of sub-samples through a first separation protocol using the microtiter plate 500, the technician may perform a second separation protocol. Through the second separation protocol, one or more of the sub-samples may be further separated into a plurality of mini-samples.

Figure 8A:
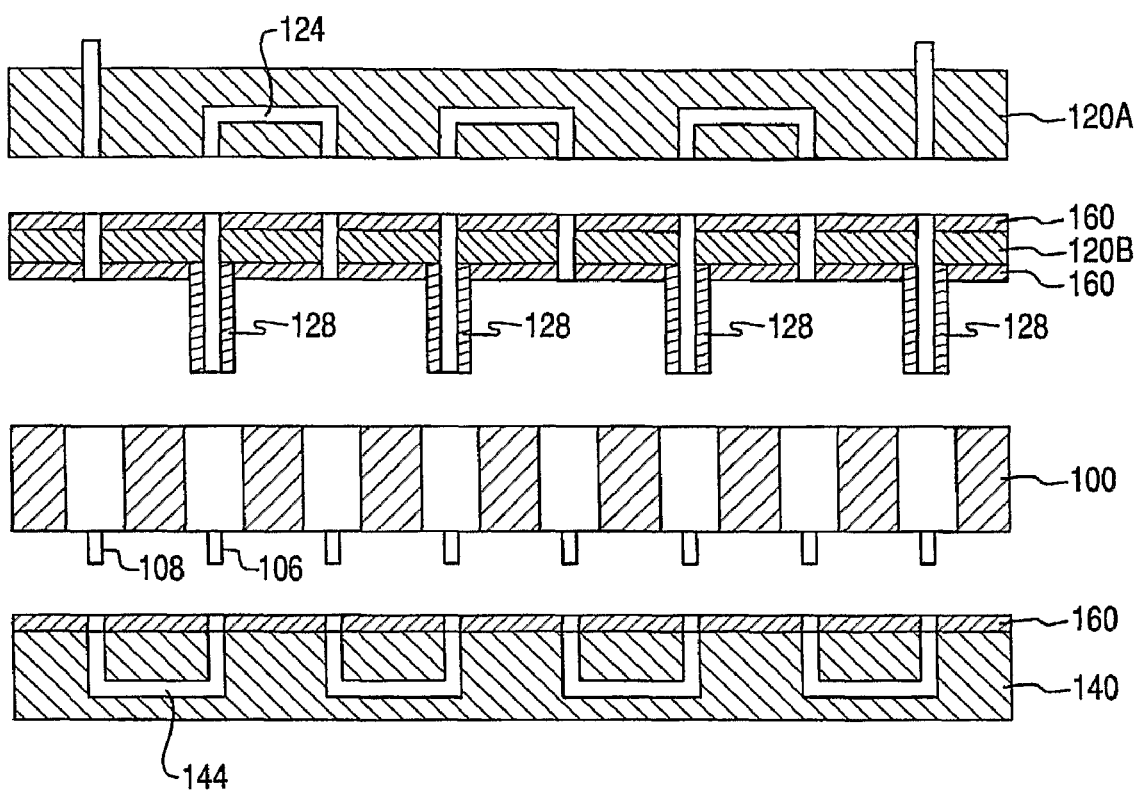
FIG. 8A is a cross-sectional view of a third embodiment in which an upper plate of the embodiment of FIGS. 1-4 is divided into two separate pieces, thereby enabling the embodiment to act in the manner of the embodiment shown in FIGS. 5-7.

FIG. 8A is a cross-sectional view of an alternate embodiment in which the upper plate 120 of the embodiment to FIGS. 1-4 is divided into two separate pieces 120A, 120B, thereby creating a device that has a similar top-to-bottom functionally as the embodiment shown in FIGS. 5-7. More specifically, long capillary portions 128 of the lower piece 120B are configured to pass entirely through a chamber 102, i.e., each long portion 128 essentially enables a sample to bypass the chamber 102 in which the long portions 128 is provided. In other words, as a result of the long capillary portions 128, a sample may pass from an outlet 108 of a first chamber, through a conduit 144 in the lower plate 140 and directly through a second chamber 102 in which the long portion 128 is positioned. As a result, the sample can directly pass to the inlet 106 of a third chamber 102 (via a conduit 124 in the upper plate 120A). Accordingly, this embodiment is a top-to-bottom device similar to that shown in FIGS. 5-7.

In a further version of the embodiment shown in FIG. 8A, one or more gaskets 160 may be provided (as shown) to enhance the seal between the various plates 120A, 120B, 100, 140.

Figure 8B:
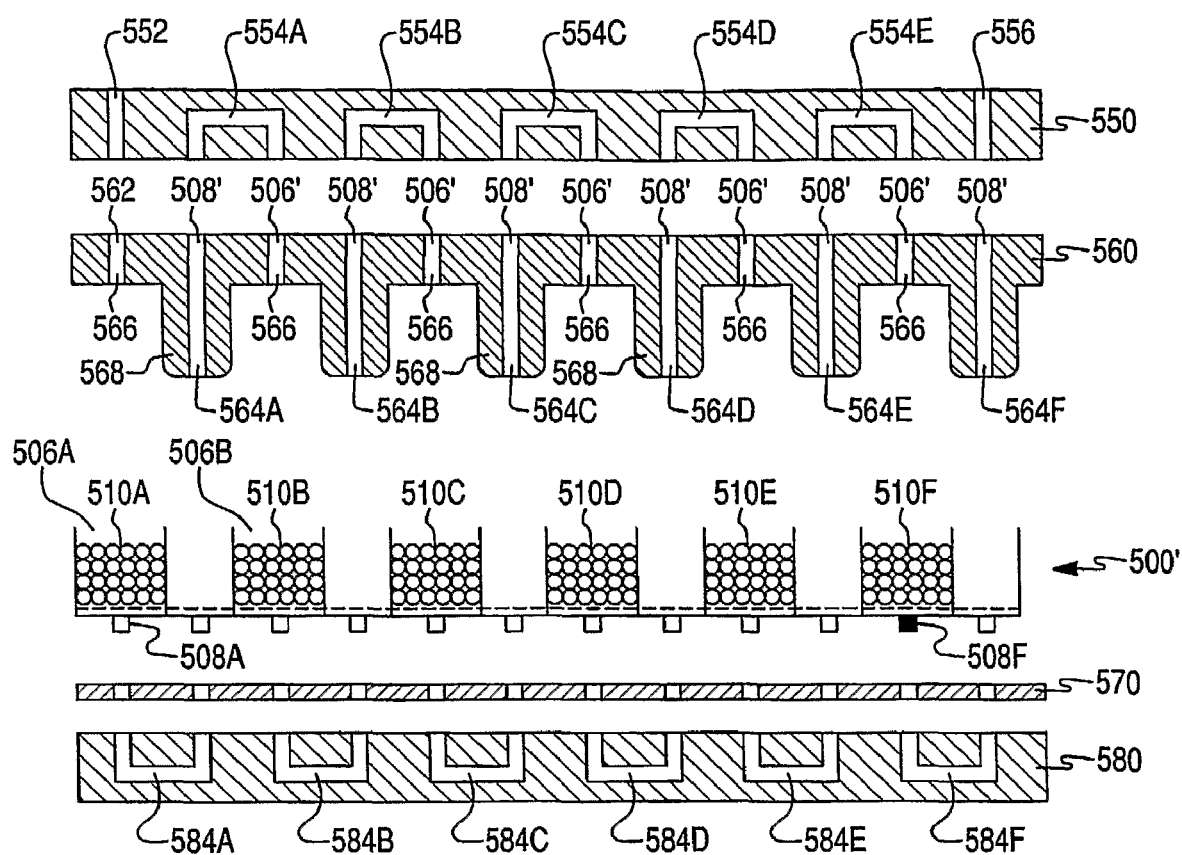
FIG. 8B is an alternate embodiment of the microtiter plate shown in FIG. 8A.
Figure 9A:
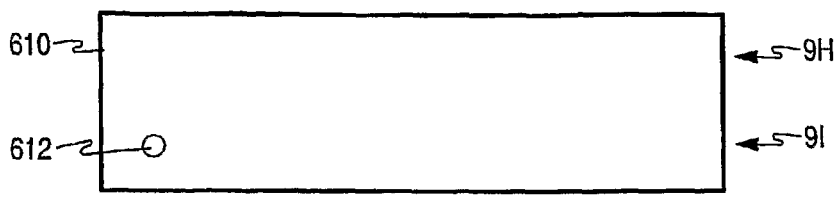
FIG. 9A is a top view of a top cover plate according to a fourth embodiment of the present invention.
Figure 9B:
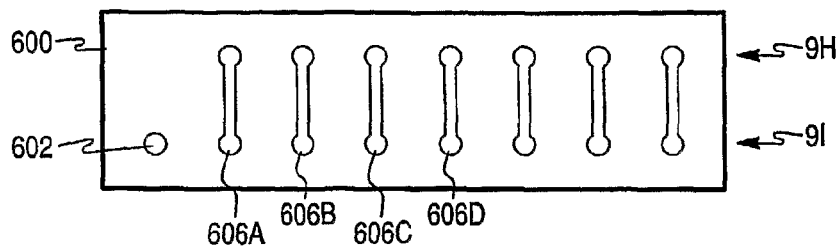
FIG. 9B is a top view of a top conduit plate according to a fourth embodiment of the present invention.
Figure 9C:
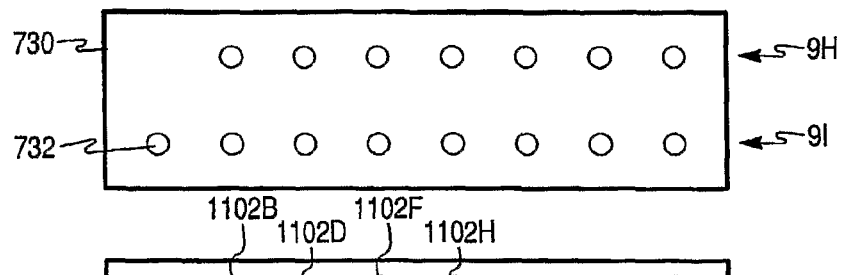
FIG. 9C is a top view of a top gasket plate according to a fourth embodiment of the present invention.
Figure 9D:
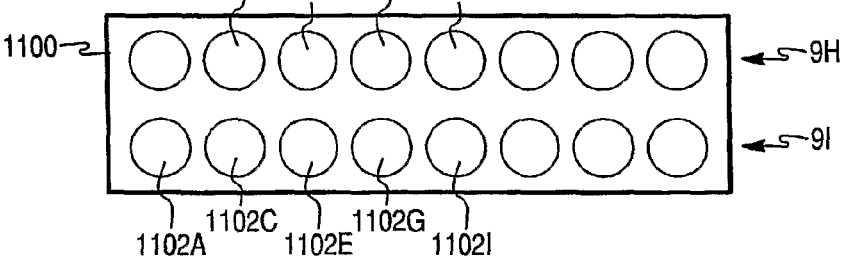
FIG. 9D is a top view of a microtiter plate, which contains two rows of chambers and which may be used in a fourth embodiment of the present invention.
Figure 9E:
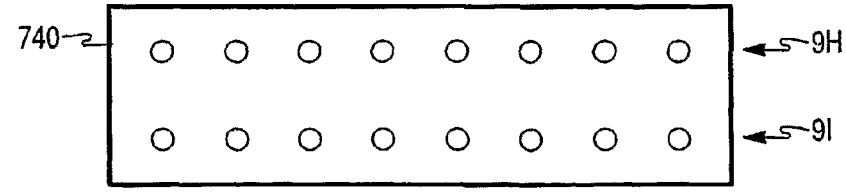
FIG. 9E is a top view of a bottom gasket plate according to a fourth embodiment of the present invention.
Figure 9F:
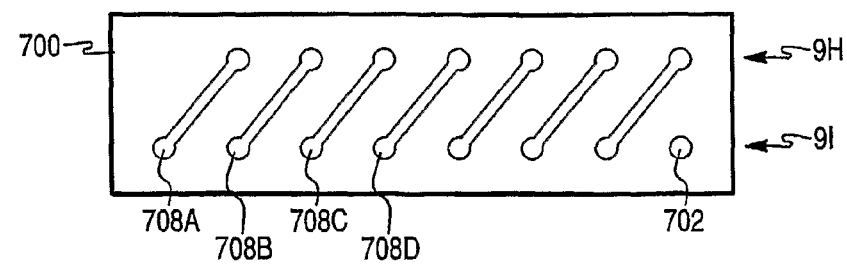
FIG. 9F is a top view of a bottom conduit plate according to a fourth embodiment of the present invention.
Figure 9G:
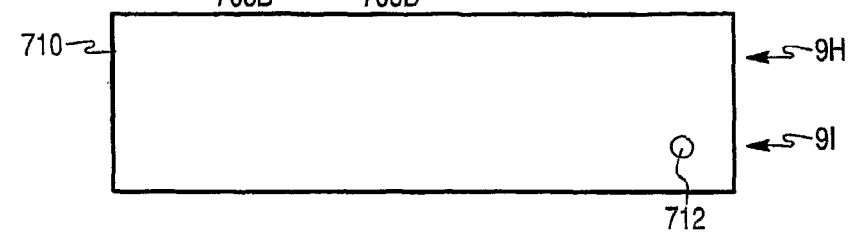
FIG. 9G is a top view of a bottom cover plate according to a fourth embodiment of the present invention.
Figure 9H:
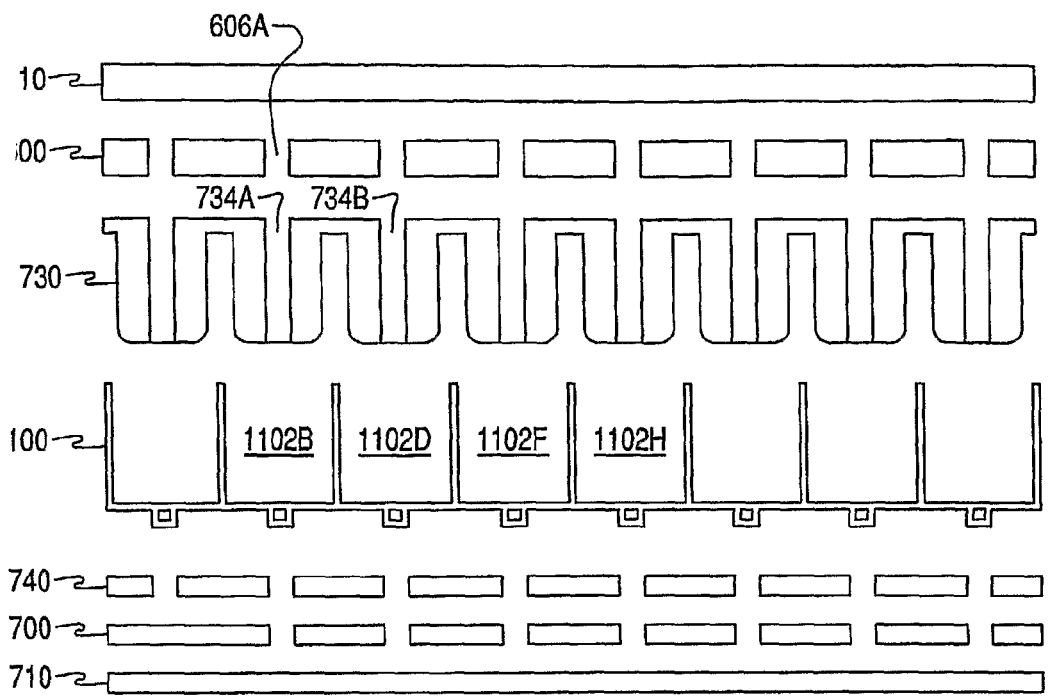
FIG. 9H is a side, cross-sectional view of the plates of FIGS. 9A-9G taken along lines indicated by arrows 9H.
Figure 9I:
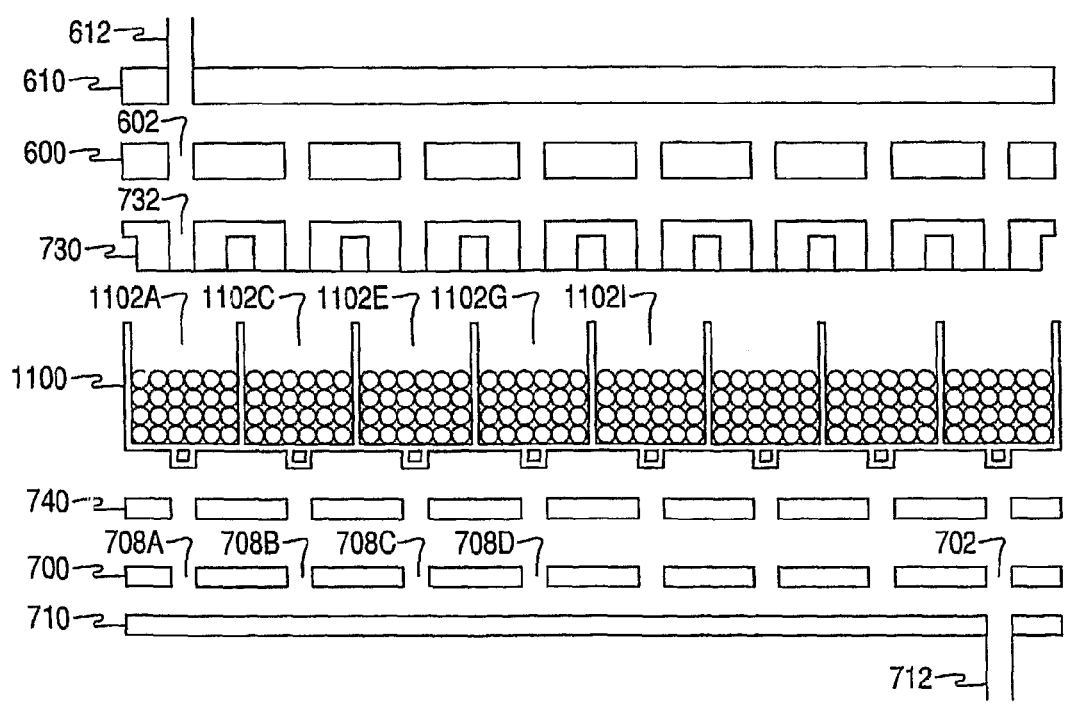
FIG. 9I is a side, cross-sectional view of the plates of FIGS. 9A-9G taken along lines indicated by arrows 9I.

FIG. 8B shows an alternate embodiment plate 500'. Like the embodiment shown in FIG. 8A, in this embodiment, the conduits 502 of the embodiment shown in FIGS. 5-7 are replaced by a series of plates 550, 560, 580, which are shown as being separated for ease of understanding. In use, the plates 500, 550, 560, 580 would be sandwiched together to create a top-to-bottom fluid pathway that, like the embodiment shown in FIG. 8A, is generally in the shape of a square-wave.

In this alternate embodiment, an upper plate 550 contains an inlet port 552, a plurality of conduits 554, and an outlet port 556. The inlet port 552 is configured to align with the an inlet 562 of an inlet channel 566 of a channel plate 560 and, in turn, with an inlet 506A of a first chamber 510A in a linear series. Similarly, the outlet port 556 is configured to align with an outlet 508' of an outlet channel 564 of the channel plate 560 and, in turn (via a conduit 584F below described) with an outlet 508F of a last chamber 510F in the linear series. The conduits 554 in the upper plate 550 are configured to connect outlets 508' of outlet channels 564 to inlets 506' of inlet channels 566 in the channel plate 560. A lower plate 580, which contains a plurality of conduits 584, is positioned on the other side of the microtiter plate 500'. As a result, a sample can pass: (a) from the outlet 508A of, e.g., the first chamber 510A, (b) though a conduit 584A in the lower plate 580 to an outlet channel 564A in the channel plate 560, (c) through the outlet channel 564A, (d) through a conduit 554A in the upper plate 550, and (e) into the inlet 506B of a second chamber 510B. As a result, the sample takes a top-to-bottom (generally square-wave shaped) path through each of the chambers 510.

In contrast to the long capillary portions 128 of the embodiment shown in FIG. 8A, in this embodiment, chamber portions 568 of the channel plate 560 are sized to substantially fill chambers, which serve as channels, in the microtiter plate 500'. As a result, each of the outlet channels 564 in the channel plate 560 may be have a diameter that is different than the diameter of the long capillary portions 128 of the embodiment shown in FIG. 8A. Moreover, as a result of the chamber portions 568, the system may enjoy better overall sealing conditions.

In should be readily recognized that this embodiment microtiter plate 500' can also employ a gasket 570 (as shown). Moreover, the top and bottom plates 550, 580 could be formed in multiple parts, which would facilitate cleaning of the conduits 554, 584 therein.

Similar to the aforementioned embodiments, when a technician has separated a sample into a plurality of sub-samples through a first separation protocol using the microtiter plates of the embodiments shown in FIG. 8A or 8A, the technician may perform a second separation protocol. Through the second separation protocol, one or more of the sub-samples may be further separated into a plurality of mini-samples.

FIGS. 9A-9I depict another embodiment of the present invention. In this embodiment, a plate 1100 (FIG. 9D), which contains a plurality of chambers 1102, may be combined with an upper cover plate 610 (FIG. 9A), an upper conduit plate 600 (FIG. 9B), a lower conduit plate 700 (FIG. 9F), and a lower cover plate 710 (FIG. 9G) to create a flow path through a plurality of chambers 1102A-1102I that are positioned in two adjacent rows. In addition, a channel plate 730 (FIG. 9C) may be provided between the plate 1100 and the upper conduit plate 600. Similarly, a gasket 740 (FIG. 9E) may be provided between the plate 1100 and the lower conduit plate 700.

In this embodiment, an inlet port 612 in the upper cover plate 610 may be aligned with an inlet port 602 in the upper conduit plate 600 and an inlet port 732 in the channel plate 730. Together, the inlet ports 602, 612, 732 may form an inlet to a first chamber 1102A in a first row R1. A sample supplied to the first chamber 1102A (via the inlet ports 602, 612, 732) may pass top-to-bottom through the first chamber 1102A and into a first diagonal conduit 708A in the lower conduit plate 700. From the first diagonal conduit 708A, the sample (or portion thereof) may flow into a channel 734A in a second chamber 1102B (which may or may not have a separation medium therein) that is in a second row R2, which is behind the first row R1. After passing bottom-to-top through the channel 734A in the second chamber 1102B, the sample (or portion thereof) may flow through a first transverse conduit 606A (in upper conduit plate 600) to a third chamber 1102C that, like the first chamber 1102A, is in the first row R1. The sample may then pass top-to-bottom through the third chamber 1102C and continue on this front-to-back/bottom-to-top, back-to-front/top-to-bottom path until it reaches a final chamber 1102I, which (as shown) may be in the first row. The sample (or portion thereof) may then be removed from the final chamber 1102I by way of outlet ports 702, 712 formed in the lower conduit plate 700 and the lower cover plate 710, respectively. Together the outlet ports 702, 712 may serve as an outlet.

In some embodiments, the upper cover plate 610 and the upper conduit plate 600 may be integrally formed. Additionally or alternatively, the lower cover plate 710 and the lower conduit plate 700 may be integrally formed.

Figure 10:
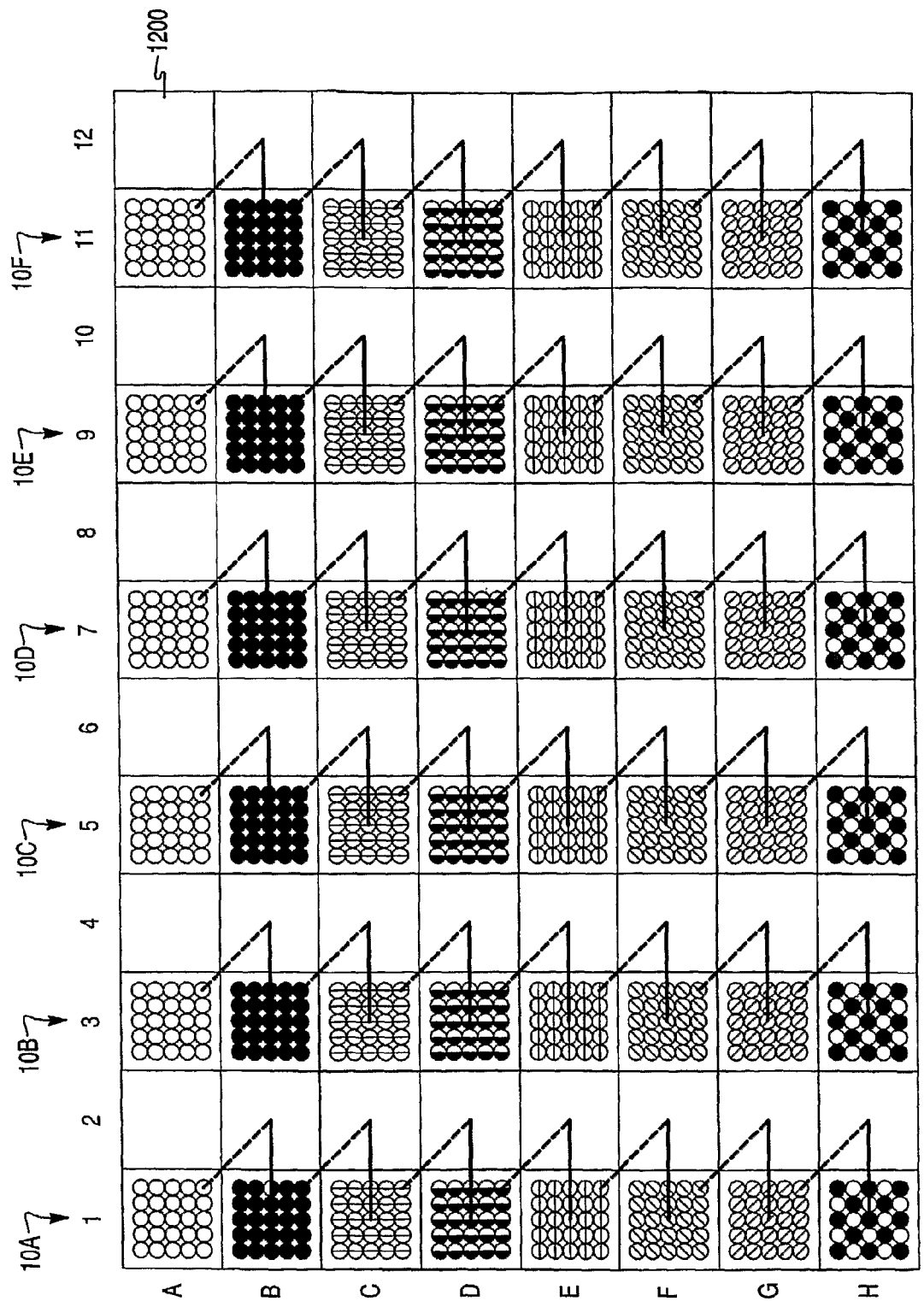
FIG. 10 is top view of multiple sample pathways arranged side-by-side.

Another related embodiment of the invention is shown in FIG. 10. In this case, each chamber in a first linear series of chambers (e.g., a column or a row) in a plate 1200 contains a separation medium through which a sample flows in the same direction (e.g., top-to-bottom), and the chambers in an adjacent linear series serve as channels though which the sample flows in the opposite direction (e.g., bottom-to-top). In this embodiment, for example, a conduit, such as a tube, may be connected the outlet at the bottom of a first chamber 1A in a first linear series, may pass up through a second chamber 2B in a second linear series, and may connect to the inlet at the top of third chamber 1B in the first linear series. Another conduit may connect the outlet at the bottom of the third chamber 1B, pass up through a fourth chamber 2C in the second linear series, and may connect to the inlet at the top of a fifth chamber 1C in the first linear series, and so forth. The diagonal arrangement of the conduits can be located at the top of the plate (similar to the embodiment shown in FIGS. 9A-9I), if desired.

Although FIG. 10 shows multiple separation protocols 10A-10F on the same plate 1200, this parallel functionality is not exclusive to this embodiment. Rather, any of the previously described embodiments may, like that of the embodiment shown in FIG. 10, involve parallel separation protocols on one plate.

In some alternate embodiments of any of the aforementioned embodiments, the flow directions across the various separation media may be operated in packed-bed format, fluidized-bed format, or a combination of packed-bed and fluidized-bed, depending on the configuration of the connection conduits.

It should be readily recognized that the separation media are not limited to any particular type. Rather, the separation media can be of any type of including, but not limited to solid materials (both porous and non-porous) such as beads, irregular particles, membranes, monoliths, etc.

By way of example, a sample solution, which contains a complex mixture that includes a plurality of different biomolecular components, may be introduced into a first chamber 102/510 in a series of chambers for at least partial resolution as described hereinbelow. Each of the chambers 102/510 through which the sample passes may, e.g., include a different sorbent material. More specifically, the sorbent materials may be chosen such that substantially all of the distinct biomolecular components of the sample are captured by the various sorbents in the chambers 102/510. After the capture of the various subsets of the plurality of biomolecular components, the sorbents, including the captured biomolecular components, may be isolated (i.e., removed from the chambers) or otherwise removed for further processing, as previously discussed.

As used herein "capture" refers to the capacity of a sorbent to attract and reversibly retain one or more biomolecular components in a sample solution such that certain subsets-samples of the biomolecular components are substantially completely removed from the sample solution during passage through the chambers 102/510. Those of skill in the art of separating mixtures of chemicals of biological origin, such as protein purification, will appreciate that a sorbent's capacity to retain a biomolecular component inherently includes a specificity of the sorbent for certain biomolecular components that is defined by the interaction between the sorbent and a biomolecular component under the ambient conditions in which the sorbent and the solution are in contact (e.g., the temperature and ionic strength or pH of the solution being passed through the chambers 102/510). The interaction can be any physicochemical interaction known or believed to be sufficient to cause sorption of a biomolecular component (or subset-sample of biomolecular components) by the sorbent to substantially completely deplete the solution of the biomolecular component (or subset-sample), but still allow subsequent elution of the captured biomolecular component(s).

Typical sorbent-biomolecular component interactions include without limitation: ion exchange (cation or anion); hydrophobic interactions; biological affinity (including interactions between dyes and ligands with proteins, or lectins with glycoconjugates, glycans, glycopeptides, polysaccharides, and other cell components); immunoaffinity (i.e., antigen-antibody interactions or interactions between fragments thereof); metal-chelate or metal-ion interactions, interactions between proteins and thiophilic materials, interactions between proteins and hydroxyapatite, and size exclusion. Many such materials are known to those having skill in the art of protein or nucleic acid purification. These materials can be made using known techniques and materials or purchased commercially. Descriptions of these materials and examples of methods for making them are described in "Protein Purification Protocols" 2d Edition, Cutler, Ed. Humana Press 2004, which is incorporated herein by reference in its entirety for all purposes.

Ion exchanging materials include strong and weak cation- and anion exchange resins. Strong, some of which are later listed in Table 4. Examples of strong cation exchanging ligands include sulfopropyl (SP) and methyl sulfonate (S). WeakExamples of weak cation exchange ligands include carboxymethyl (CM). StrongExamples of strong anion exchange ligands include quaternary ammonium and quaternary aminoethyl (QAE). WeakExamples of weak anion exchange ligands include diethylaminoethyl (DEAE). Examples of suitable ion-exchange materials include without limitation, the materials sold commercially under the trade names: Q-, S-, DEAE- and CM CERAMIC HYPERD®; DEAE-, CM-, and SP TRISACRYL®; M-, LS-; DEAE-, and SP SPHERODEX® LS; and QMA SPHEROSIL® LS from Pall Corporation (East Hills, N.Y. (Fremont, Calif.). Other suitable ion exchanging materials are sold under the trade names: UNOSPHERE, MACRO-PREP (including HIGH Q, HIGH S, DEAE, and CM), and AG and Bio-Rex from Bio-Rad Laboratories of Hercules, Calif. Still more suitable commercially available ion exchange materials are sold under the trade names: DEAE-TRISACRYL®, DEAE SEPHAROSE®, DEAE-CELLULOSE, DIETHYLAMINOETHYL SEPHACEL®, DEAE SEPHADEX®, QAE SEPHADEX®, AMBERJET®, AMBERLITE®, CHOLESTYRAMINE RESIN, CM SEPHAROSE®, SP SEPHAROSE®, SP-TRISACRYL®, CELLULOSE PHOSPHATE, CM-CELLULOSE, CM SEPHADEX®, SP SEPHADEX®, and AMBERLITE® from Sigma-Aldrich Co. (St. Louis, Mo.). Other commercial sources for ion exchange materials include Amersham Biosciences (www.amersham.com). Still other materials will be familiar to those having skill in the art of protein purification.

Materials suitable for exploiting hydrophobic interactions (hydrophobic interaction chromatography, "HIC") include those sold under the trade names: PHENYL SEPHAROSE 6 FAST FLOW, BUTYL SEPHAROSE 4 FAST FLOW, OCTYL SEPHAROSE 4 FAST FLOW, PHENYL SEPHAROSE HIGH PERFORMANCE, PHENYL SEPHAROSE CL-4B, OCTYL SEPHAROSE CL-4B, SOURCE™ 15ETH, SOURCE 15ISO, and SOURCEPHE from Amersham Biosciences of Piscataway, N.J. Also available are materials sold as FRACTOGEL® EMD PROPYL (S) AND FRACTOGEL® EMD PHENYL I (S) from VWR International (www.chromatography.uk.co). Still other commercially available HIC materials include the materials sold under the trade names: TOYOPEARL and TSKGEL from Tosoh Bioscience LLC of Montgomeryville, Pa. An equivalent material is sold commercially under the trade name MEP HYPERCEL by Pall Corporation (East Hills, N.Y.). Still other materials will be familiar to those having skill in the art of protein purification.

Affinity materials include any materials effective to attract and sorb biomolecular components on the basis of structural interactions between a biomolecular component and a ligand such as: antibody-antigen, enzyme-ligand, nucleic acid-binding protein, and hormone-receptor. The interactions can be between naturally occurring or synthetic ligand and a biomolecular component. The ligands can be either mono-specific (e.g., a hormone or a substrate) or group-specific (e.g., enzyme cofactors, plant lectins, and Protein A). Examples of common group-specific ligands suitable for the present invention are provided in Table 1.

TABLE 1

| Ligand(s) | Target(s) |
| --- | --- |
| 5'-AMP, 5'-ATP | Dehydrogenases |
| NAD, NADP | Dehydrogenases |
| Protein A | Immunoglobulins |
| Protein G | Immunoglobulins |
| Lectins | Polysaccharides, Glycoproteins |
| Histones | DNA |
| Heparin | Lipoproteins, DNA, RNA, clotting factors |
| Gelatin | Fibronectin attachment factors |
| Lysine | rRNA, dsDNA, Plasminogen |
| Arginine | Fibronectin attachment factors |
| Benzamidine | Serine proteases |
| Polymyxin | Endotoxins |
| Calmodulin | Kinases |
| Cibacron Blue | Kinases, Phosphatases, Dehydrogenases, Albumins |
| Boronic Acid | Biomolecules containing cis-diols (RNA, glycoproteins) |

Thus, a wide variety of biomolecular materials can be sorbed using affinity materials. Commercially available affinity materials include those sold under the trade names: PROTEIN A CERAMIC HYPERD®, BLUE TRISACRYL® M, HEPARIN HYPERD® M, and LYSINE HYPERD® from Pall Corporation (East Hills, N.Y.). Still other commercially available materials are provided by commercial suppliers including Amersham Biosciences (www.amershambiosciences.com) and Sigma-Aldrich (www.sigmaaldrich.com). Still other materials will be familiar to those having skill in the art of protein purification.

In some embodiments of the invention, the affinity materials are derived from reactive dyes are used to create sorbents. Dye-ligand sorbents are often useful for binding proteins and enzymes that use nucleic acid cofactors, such as kinases and dehydrogenases. But, other proteins, including serum albumins, can be sorted efficiently with these sorbents as well. Examples of suitable commercially available materials include those sold under the trade names REACTIVE BLUE, REACTIVE RED, REACTIVE YELLOW, REACTIVE GREEN, and REACTIVE BROWN (Sigma-Aldrich); DYEMATRIX GEL BLUE, DYEMATRIX GEL RED, DYEMATRIX GEL ORANGE, and DYEMATRIX GEL GREEN (Millipore, Billerica, Mass.); and the Procion dyes known as Blue H-B (Cibacron Blue), Blue MX-R, Red HE-3B, Yellow H-A, Yellow MX-3r, Green H-4G, Green H-E4BD, Brown MX-5BR. Still others will be familiar to those having skill in the art of protein purification.

Useful sorbents can also be constructed from lectins to separate and isolate glycoconjugates, glycans, glycopeptides, polysaccharides, soluble cell components, and cells. Suitable lectins include those shown in Table 2.

TABLE 2

| Lectin | Use(s) |
| --- | --- |
| Concanavalin A | Separation of glycoproteins, glycoprotein enzymes, and lipoproteins; isolation of IgM |
| Lens culinaris | Isolation of gonadotropins, mouse H antigens, detergent-solubilized glycoproteins |
| Tritium vulgaris | Purification of RNA polymerase transcription cofactors |

TABLE 2-continued

| Lectin | Use(s) |
| --- | --- |
| Ricins communis | Fractionation of glycopeptide-binding proteins |
| Jacalin | Purification of C1 inhibitors, separation of IgA1 and IgA2 |
| Bandeira simplicifolia | Resolution of mixtures of nucleotide sugars |

Commercially available lectins include those sold under the trade names: AFFI 10, AFFI 15, AFFI PREP 10, and AFFI PREP 15 (Bio-Rad, Hercules, Calif.); CNBR ARGINOSE, EPOXY-ACTIVATED ARAGROSE, CDI AGAROSE, and POLYACRYLHYDRAZIDE AGAROSE (Sigma-Aldrich, St. Louis, Mo.); and REACTI 6X (Pierce, Rockford, Ill.).

Immunoaffinity materials can be made using standard methods and materials known to those having skill in the protein purification arts (see, e.g., "Protein Purification Protocols"). Commercially available immunoaffinity material include those sold by Sigma-Aldrich (www.sigmaaldrich.com) and Amersham Biosciences (www.amersham.com). Similarly, metal-ion affinity (IMAC) materials can be prepared using know materials and methods (see, e.g., "Protein Purification Protocols"), or purchased commercially (e.g., from Sigma-Aldrich (www.sigmaaldrich.com) or Amersham Biosciences (www.amersham.com)). Common metal include Ni(II), Zn(II), and Cu(II). Some examples of these materials are shown Table 3.

TABLE 3

| Chelator Ligand | Metal |
| --- | --- |
| Iminodiacetate (IDA) | Transition Metals |
| 2-Hydroxy-3-[N-(2-pyridylmethyl)glycine]propyl | Transition Metals |
| α-Alkyl nitrilotriacetic acid | Transition Metals |
| Carboxymethylated aspartic acid | $Ca^{+2}$ |
| Ethylenediamine (TED) | Transition Metals |
| $(GHHPH)_nG$* | Transition Metals |

*The letters G and H refer to standard amino acid notation: G = glycine, and H = histidine.

The synthesis of hydroxyapatite (HT/HTP) and thiophilic (TAC) sorbents will also be familiar those having skill in the protein purification arts (see, e.g., "Protein Purification Protocols"). Commercial sources include Bio-Rad of Hercules, Calif. (trade name CHT), Pall Corporation (East Hills, N.Y.) (trade name HA ULTROGEL®, and Berkeley Advanced Biomaterials of San Leandro, Calif. (trade name HAP). Thiophilic sorbents also can be made using methods and materials known in the art or protein purification or purchased commercially under the trade names: MEP HYPERCEL (Ciphergen Biosystems, Fremont, Calif.), THIOPHILIC UNIFLOW and THIOPHILIC SUPERFLOW (Clonetech, Palo Alto, Calif.), THIOSORB (Millipore, Billerica, Mass.), T-GEL (Affiland, Ans-Liege, Belgium), AFFI-T (Ken-en-Tec, Copenhagen, Denmark), HI-TRAP (Amersham Biosciences, Piscataway, N.J.), and FRACTOGEL (Merck KgA, Poole Dorset UK).

The above-described sorbent materials have different degrees of specificity for different biomolecular components. In this regard, the term "specificity" relates to the number of different biomolecular species in a given sample that a sorbent can bind. In one aspect, sorbents can be grouped by their relative degrees of specificity, e.g., high specificity sorbents, moderate specificity sorbents, and low specificity sorbents.

High specificity materials include those materials that generally have a strong preference to sorb certain biomolecules or subsets of biomolecules. Often such materials include highly biospecific sorption interactions, such as antibody-epitope recognition, receptor-ligand, or enzyme-receptor interactions. Examples of these sorbents include Protein A-, Protein G-, antibody-, receptor- and aptamer-bound sorbents. Moderate specificity sorbents include materials that also have a degree of biospecific interactions but to a lesser degree than high specificity sorbents, and include: MEP, MBI, hydrophobic sorbents, and heparin-, dye-, and metal chelator-bound materials. Many "mixed-mode" materials have moderate specificity. Some of these bind molecules through, for example, hydrophobic and ionic interactions. Low specificity materials sorbents include materials that sorb bimolecular components using bulk molecular properties (such as acid-base, dipole moment, molecular size, or surface electrostatic potential) and include: zirconia, silica, phenylpropylamine cellulose, ceramics, titania, alumina, and ion exchangers (cation or anion).

In one embodiment of the invention, the solution of biomolecular components may be contacted with at least two different sorbents from among high-, moderate-, or low-specificity sorbents. In some embodiments, the solution will be contacted with one, two, or three or more materials of the same degree of specificity (e.g., two materials of moderate specificity or three materials of low specificity). In another embodiment, the solution may be contacted with a plurality of sorbents that define a progression from high specificity to low specificity. In another embodiment, the solution may be contacted with a plurality of sorbents that define a progression from high specificity to low specificity. In yet another embodiment, the sorbent materials may be arranged to provide a substantially linear progression of specificities. In still another embodiment, the sorbent materials may form a substantially contiguous body. In still another embodiment, the sorbents may be mutually orthogonal, i.e., the capacity of each sorbent may be substantially selective for a unique biomolecular component or subset of biomolecular components. In another embodiment, the sorbents may be chosen such that at least one sorbent is a high specificity sorbent and at least one other sorbent is either a moderate- or low specificity sorbent. In yet another embodiment, the sorbents may be chosen such that at least one sorbent each is a high specificity sorbent, a moderate specificity sorbent, and low specificity sorbent. In still another embodiment, at least two sorbents may be chosen from two classes of high specificity sorbents, moderate specificity sorbents, and low specificity sorbents. In another embodiment, at least two sorbents may be high specificity sorbents and at least one sorbent may be a low specificity sorbent.

The progression from high specificity to low specificity serves a particularly useful purpose. In particular, it allows fractionation of the proteins in the sample into largely exclusive groups, but of decreased complexity. As such, the proteins in the various fractions may be more easily resolved. For example, a low- or moderate-specificity resin might have affinity for or bind to many biomolecules in a sample, including ones in very high concentration. However, by exposing the sample to a high specificity sorbent that is directed to the protein in high concentration before exposing to the moderate-specificity sorbent, one can remove most or all of the high concentration protein. In this way, the set of biomolecules captured by the moderate specificity sorbent will largely or entirely exclude the high concentration biomolecule. This results in a less complex set of proteins captured by the moderate specificity sorbent. The strategy, thus, is to remove at earlier stages biomolecules, e.g., proteins, that would otherwise be captured by sorbents at later stages of the fractionation process so that at each chamber 102/510, the complexity of the biomolecules passing to the next chamber 102/510 is decreased.

In one embodiment, the sorbents may be chosen such that the biomolecular materials of the greatest concentrations are removed first. For example, arranging the sorbents such that a Protein A sorbent and a Cibacron Blue sorbent are the first two sorbents can reduce the dynamic range of human serum. Ninety percent of the protein composition of human serum includes: albumin, IgG, transferrins, $\alpha$-1 anti-trypsin, IgA, IgM, fibrinogen, $\alpha$-2-macroglobulin, and complement C3. Of the remaining 10%, about 99% includes: apolipoproteins A1 and B; lipoprotein A; factor H; ceruloplasm; pre-albumin; complement factor B; complement factors C4, C8, C9, and C19; and $\alpha$-glycoprotein. Often, placing a sorbent such as phenylpropylamine cellulose in the last chamber 102/510 is useful to catch any remaining biomolecular components in the sample. Generally, if the initial sorbent(s) are too general (i.e., have low specificity), then too much material can be sequestered with the first two sorbents, which degrades the usefulness of the remaining sorbents. However, if the initial sorbents are too specific (i.e., have high specificity), then the efficiency of the remaining sorbent materials can be reduced by a large sample dynamic range. In one embodiment, the sorbents are chosen such that the first sorbent, or first and second sorbents combined, provide a reduction in the dynamic range of the sample by a factor of at least 10, more specifically a factor of at least 100, and, still more specifically a factor of at least 1,000.

The multiplex separation methods of this invention are particularly useful for fractionating analytes in complex mixtures, e.g., samples comprising at least 1000, at least 100,000 or at least 10,000,000 different biomolecular species (e.g., proteins). The methods of this invention are particularly useful for separating biomolecules from biological samples. Such samples can include, for example, amniotic fluid, blood, cerebrospinal fluid, intraarticular fluid, intraocular fluid, lymphatic fluid, milk, perspiration plasma, saliva semen, seminal plasma, serum, sputum, synovial fluid, tears, umbilical cord fluid, urine, biopsy homogenate, cell culture fluid, cell extracts, cell homogenate, conditioned medium, fermentation broth, tissue homogenate and derivatives of these.

An advantage of the present invention is that the device may be used for, and is to use and readily adaptable to, any desired number of separations. Moreover, other than some basic lab equipment, including, e.g., a peristaltic pump and/or a vacuum station, no additional equipment may be needed.

In another embodiment the device of this invention is used to apply a two-dimensional separation method to a mixture of analytes in a sample. Conceptually, this method involves two steps. A first step involves fractionating analytes into a set of first aliquots based on degree of a first physical-chemical property using a plurality of first sorbents. By choosing appropriate sorbents, the analytes can be partitioned so that each fraction or aliquot contains analytes falling within a particular range. A second step involves then fractionating the aliquots (or at least one aliquot) into a set of second aliquots based on degree of a different second physical-chemical property using a plurality of different second sorbents. Then, the second aliquots can be further analyzed to achieve yet a third dimension of fractionation by, for example, mass spectrometry. By "physical-chemical property" is meant a property of analytes which can be measured and which can serve as the basis for analyte separation. Preferably, the physical-chemical property used in this method is one that varies by degree. For example, proteins are characterized by isoelectric point, which is one physical-chemical property, and which is measured on a scale from low pI (e.g., pI 3) to high pI (e.g., pI 10). As is well known in the art, proteins can be separated based on isoelectric point using, for example, isoelectric focusing or ion exchange chromatography. Hydrophobic index is another physical-chemical property that characterized analytes (polypeptide analytes in particular) and which can be measured on a scale from low hydrophobic index to high hydrophobic index. As is also well known in the art, proteins can be separated based on hydrophobic index using hydrophobic (reverse phase) sorbents or normal phase sorbents. Another physical-chemical property which can be used to fractionate proteins is size, and gel permeation chromatography (size exclusion chromatography) is useful for this purpose. Another physical-chemical property which can be used to fractionate proteins is metal binding ability. In this case, a series of metal chelate sorbents charged with different metals can be used. Mass is another physical-chemical characteristic of polypeptide analytes that can be the basis for separation. However, mass spectrometry and gel electrophoresis are preferred over chromatography for this purpose.

Methods for three-dimensional separation are known in the art. One example is LC-LC-MS. However, one drawback of this method is that it typically involves sequential elution of analytes from separation media, which can be time consuming. This can involve changing buffer systems to achieve differential elution of analytes from a sorbent. Existing attempts to multiplex this method can involve using multiple chromatography columns in parallel, which can become very costly. However, by combining the device of this invention with chromatographic media that use compatible water-based solvent systems, both the time and the cost impediments can be significantly improved.

A preferred embodiment of this invention involves using pI and hydrophobicity as the two dimensions on which the analytes are chromatographically separated, followed by separation based on mass using mass spectrometry. This method conveniently uses solid buffers for pI separation and hydrophobic sorbents for separation by hydrophobic index. Solid buffers are described in U.S. provisional patent application 60/702,989, filed Jul. 28, 2005 ("Separation of proteins based on isoelectric point using solid-phase buffers" Boschetti et al.). They are particularly useful here because they separate according to pI without resort to electrophoretic separation or different buffer systems to achieve step-wise pI fractionation. Any series of reverse phase sorbents can be used. Many of these are commercially available. Another sorbent that is useful for hydrophobic separation under physiological conditions is described in International Publication Number WO 2005/073711 ("Chromatographic material for the adsorption of proteins at physiological ionic strength," Boschetti et al.) The arrangement of hydrophobic materials in series from least hydrophobic to most hydrophobic for the separation of analytes is also described in U.S. provisional patent application 60/591,319, filed Jul. 27, 2004 ("Multichemistry fractionation," Guerrier). All of these documents are incorporated herein by reference.

One method proceeds as follows. A plurality of compartments in one row (or column) of the device of this invention are filled with chromatographic materials that bind analytes based on isoelectric point. For example, a solid phase buffer can be used. The materials are arranged so that the flow of fluid passes the sample mixture through a series of sorbents that bind the analytes from high to low pI (or, conversely, from low to high pI) and, therefore, from most specific to least specific. For example, the first sorbent in the series can capture, and therefore remove, all proteins having a pI above 9. A second sorbent can capture all proteins having a pI above 7. This sorbent will, therefore, partition those proteins the pI of which is between 7 and 9. A sorbent in a subsequent compartment in the series can capture proteins having a pI above 5 and, therefore, will partition those proteins whose pI is between 5 and 7. And so on.

In a next step, the fluid conduits of the device are re-routed so that instead of connecting compartments in a row series, they now connect each compartment in the row with compartments in a column. (Conversely, if the first separation is in a column, then the conduits are rerouted into rows.) A series of compartments in each column is filled with a series of reverse phase sorbents, each sorbent in the series being more hydrophobic (and, therefore, less specific) than the previous one. A buffer is now pumped through the conduits so that the analytes captured on each of the isoelectric sorbents passes sequentially though the series of hydrophobic sorbents. For example, the hydrophobic sorbents buffers in the series can comprise a $C_4$ chain, a $C_8$ a chain, $C_{12}$ chain, $C_{18}$ chain. This results in a plurality of aliquots, each of which is defined by a particular pI range and hydrophobic index range.

This method of two-dimensional separation need not be performed entirely on the device of this invention, or on using the device of this invention at all. For example, one can separate analytes in a first dimension using the device of this invention and then perform the separation in the second dimension using a different device. In one such embodiment, after partition of the analytes in a first dimension, the liquid conduits can be removed and the device can be placed on a stack of drip plates or separatable columns so that the outlets of the compartments align with the wells of the plates or columns. Each well of a plate in the stack that is aligned under an outlet of the device can be filled with one of the series of chromatographic materials that captures based on the second separation dimension. Thus, for example, the device of this invention can have compartments arranged into 96 well format, having 8 rows, A-H and twelve columns, 1-12. In a first separation, the compartments of column 1, e.g. compartments 1A to 1H, can be used to perform the first separation. Then, the device can be placed on top of a stack of eight filter plates (plates 1-8) also in 96 well format, with compartment/well 1A of all the plates aligned vertically under compartment 1A of plate stack. The wells of column 1 in each plate would contain the same chromatographic material for the second separation dimension and they typically would be ordered from most selective at the top to least selective at the bottom. Elution buffer is then pumped through the stack, passing though all wells 1A, all wells 1B, etc. in parallel. The result would be an 8×8 separation set in the wells of the plates. The captured analytes can then be eluted from each of these sixty-four wells for further analysis, e.g., separation of the analytes by mass on, e.g., a mass spectrometer.

Alternatively, the two-dimensional separation just described can be performed on any device or combination of devices in which the chromatographic media are physically separate and able to separately sequester the analytes. For example, the method could be performed entirely on drip plates in the 96-well format. In one such embodiment the first series of chromatographic materials could be placed into well 1A of each of eight different filter plates. These plates could be stacked on top of each other in the appropriate order and the sample could be deposited in the first well on the top of the stack that contained the most specific chromatographic material for the first separation dimension (for example, a solid buffer with pI 10 further comprising an anion exchanger). Then, buffer could be pumped through the column of wells 1A of the eight stacked plates and analytes would be appropriately sequestered according to the first physical-chemical characteristic (in this example, pI). Eluate could be collected from the bottom plate. Now, each of these plates could be independently stacked on top of a stack of filter plates in which well 1A was filled with a series of chromatographic materials ordered to separate the analytes according to the second physical-chemical characteristic. Again, buffer could be pumped through the column of wells 1A, fractionating the analytes in the second dimension. Then, the analyte contents of all the wells 1A could be eluted and further fractionated, e.g., by mass.

Another device that could be used for this method is a set of stackable and separatable columns. Such columns have compartments in which chromatographic media is sequestered. The are able to stack on other columns by snapping or twisting mechanisms for example.

Proteins can be separated from mixtures based on their pI using a series of the chromatographic materials of this invention, each comprising a solid buffer and an ion exchange resin. Each solid buffer comprises an amphoteric macromolecule that confers a predetermined pH to an aqueous solution. Thus, each chromatographic material produces a particular pH. Proteins passing through, and possessing a pI different from that of, the chromatographic material will have either a net positive charge or a net negative charge or be neutral, depending on whether its pI is, respectively, below, above or the same as the pH of the chromatographic material. Proteins whose charge is opposite that of the ion exchange resin at the pH of the environment bind to the ion exchanger, while neutral or same charge proteins remain unbound and pass through the chromatographic material. That is, for example, a protein that is negatively charged at the pH of the solid buffer will bind to an anion exchange resin. Then, captured proteins can be eluted from the chromatographic material. In one embodiment of the invention, a series of chromatographic materials (mixture of solid buffer and ion exchange resin), each solid buffer producing a different pH, are arranged in series. Because different proteins are charged at different pH levels, ion exchange resins of each chromatographic material in the series captures a subset of the proteins in a mixture. In this fashion, proteins from biological fluids such as serum, urine, cerebrospinal fluid (CSF), as well as soluble tissue extracts, can be separated as a function of their isoelectric point.

Chromatographic materials of this invention comprise a solid buffer in combination with an ion exchange resin. In preferred embodiments, each of these is attached to a solid phase. In particular, this invention contemplates a composition comprising solid buffer beads or particles mixed with ion exchange resin. In another embodiment, solid buffers and ion exchange resins are not attached to a solid phase. In another embodiment, buffering and ion exchange properties are associated within the same particle.

The term "solid buffer" denotes an amphoteric, cross-linked, insoluble macromolecule that is obtained from ionisable monomers, each of which has a different pK. A solid buffer confers a predetermined pH to an aqueous solution of diluted electrolytes, and it maintains the pH when acidic or alkaline molecules are added. In addition to these physico-chemical properties, a solid buffer useful in this document comprises small pores, giving the material a low exclusion limit, for example lower than 5000 Da.

A low exclusion limit prevents proteins from diffusing inside the cross-linked monomers while maintaining full diffusion for small ions. Such restricted diffusion minimizes the risk of non-specific binding to the solid buffer. In some embodiments, a solid buffer comprises an exclusion limit lower than 5000 Da, 4000 Da, or 3000 Da. Amphoteric macromolecules with small pores can be generated by using relatively concentrated monomer solutions and or high degrees of crosslinking monomers.

In one aspect, a solid buffer can be a polymer. For example, a solid buffer can be a polyacrylamide or a block copolymer. In another example, solid buffers can be made by combining acrylamide monomers of different pK to reach buffering power around at a predetermined pH.

Solid buffers can be prepared using routine chemicals and methods used in the arts of polymer chemistry and biochemistry. In general, to create a solid buffer for a particular pH, a monomer with a corresponding pK is selected (at a concentration that can range from few mM to several hundred mM) and is titrated to a pH close or same to its pK with a complementary monomer. For example, if the selected monomer has a pK of 8.0 it will be titrated to pH close to 8.0 using a monomer of a pK lower than 4.5. If a monomer of the desired pK is not available, a mixture of monomers (pK above and below the desired pK) can be used, followed by titration to a pH between the two pKs. Appropriate cross-linking reagents and polymerization catalysts are then added to the pH-adjusted solution of monomers in proportions sufficient to cause polymerization to generate particles of the solid buffer.

A variety of monomers are commercially available. Exemplarily monomers include, but are not limited to, N-acryloylglycine, 4-acrylamidobutyrric acid, 2-morpholino-ethylacrylamide, 3-morpholinopropylacrylamide, N,N-dimethylaminoethylacrylamide and N,N-dimethylaminopropylacrylamide. Immobilines also can be used to make solid buffers.

Immobilines are acrylamide derivatives that conform to the general formula:

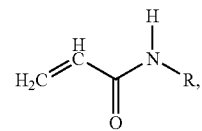

where R includes a group that provides the characteristic pI. See, e.g., U.S. Pat. No. 4,971,670. While this characterization in principle embraces many molecules, Amersham produces molecules, marketed under the trademark IMMOBILINE®, that are particularly suited for creating isoelectric gels and polymers. The IMMOBILINE® collection of molecules includes the following, having the pI indicated in parenthetical: N-acryloylglycine (pK 3.6); 4-acrylamidobutyrric acid (pK 4.6); 2-morpholinoethyl-acrylamide (pK 6.2); 3-morpholinopropylacrylamide (pK 7.0); N,N-dimethylaminoethylacrylamide (pK 8.5); and N,N-dimethylaminopropylacrylamide (pK 9.3) (collectively, "the immobilines"). Any of the immobilines can be combined, as monomers, and co-polymerized with acrylamide and N,N'-methylenebisacrylamide or another suitable cross-linking agent, to produce a desired pI specific polymer. Acrylamide can be substituted by other non-ionic acrylamide derivatives, such as N-isopropylacrylamide, methylacrylamide, methylolacrylamide dimethylacrylamide, diethylacrylamide, tris(hydroxymethyl)methylacrylamide, etc.

A variety of resources are available to assist in the selection of combinations and concentrations of monomers to produce a solid buffer with a particular pH. For example, formula tables for monomer combinations are provided in JOURNAL OF CHROMATOGRAPHIC LIBRARY, VOLUME 63 Chapter 12 (Righetti, Stoyanov & Zhukov eds., 2001). Amersham Biosciences provides similar formula tables in its "Protocol Guide #1: Isoelectric Membrane Formulas for IsoPrime Purification of Proteins." See www4.amershambioscieces.com/aptrix/upp00919.nsf/(FileDownload)?OpenAgent&docid=FD3302088BD37BC6C1256EB400417E5C&file=80635018.pdf.

Algorithms for selecting concentrations of monomers are available, too. See, e.g., Giaffreda et al., J. Chromatog., 630: 313-327 (1993). In addition, techniques for determining the pI for polymers are well-known in the art. Examples of such methods include Ribeiro et al., Computers in Biology & Medicine 20: 235-42 (1990), Ribeiro et al., loc. cit., 21: 131-41 (1991), and Sillero et al., Analytical Biochemistry 179: 319-25 (1989).

In one embodiment, the particles described in International Application PCT/US2005/007762, which is hereby incorporated by reference, can be used as solid buffers.

In another embodiment, a solid buffer is polymerized within cavities of a solid support. In other embodiments, the solid buffer is deposited on the interior and exterior surfaces of a solid support, such as the interior and exterior surfaces formed by the interior pore volume of cavities in a particle. The deposition can be by chemical bond or other means.

Amino acids and peptides can provide such surface layers, as they have defined isoelectric points. Thus, in some embodiments, a solid buffer comprises two or more amino acids. The amino acids can be any of the twenty naturally-occurring amino acids, or the amino acids can be synthetic amino acids. Useful amino acids include those among the twenty naturally occurring amino acids having ionizable side chains, including: lysine, arginine, glutamic acid, aspartic acid, serine, cysteine, threonine, tyrosine, asparagines, glutamine. In addition, it will be understood by those in the art that other compounds having defined pI values that can be attached to the interior and exterior particle surfaces as described above can be used with the present invention. Linkers can be used to provide attachment sites on the surface of a particle.

In general, a solid buffer should not be able to adsorb proteins by itself, should have the same density as the ion exchanger, and should have a good buffering capacity at the desired pH.

The term "solid support" denotes a solid, porous material wherein ion exchange polymers or solid buffers can be attached or loaded to prevent polymer collapse under low concentration.

Chromatographic material can utilize a variety of solid supports. Illustrative of solid supports in this context are particles, membranes, and monoliths. A "monolith" is a single piece of material, generally porous, to which chromatographic ligands can be attached. Generally monoliths have significantly greater volume than beads, for example, in excess of 0.5 mL per $cm^3$ of monolith.

In one embodiment, the solid support comprises a substantially porous particle having a plurality of cavities extending inwardly from the surface. The particles preferably have sizes, mechanical strengths and buoyancies that are compatible with separating biological extracts. In one embodiment, the particles comprise one or more mineral oxides such as silica, titania, zirconia, hafnia, alumina, gallia, scandia, yttria, actinia, or a rare earth mineral oxides.

When porous particles are employed as solid supports for solid buffers, relatively large particles can be used to minimize the external surface area relative to the particle volume and hence reduce the risk of non-specific binding for proteins. In some embodiments, the particles have diameters greater than about 50 μg/m, or greater than about 100 μm, or greater than about 200 μm. In one example, particles of about 150 μm are used as solid supports for solid buffers. Pore volume of the particle can range from 10 to 70% of the overall particle volume.

Alternatively, a porous, plastic bead can serve as solid support. Polystyrene is a well-known polymer that can be formed into beads having pores, for chromatography. Other synthetic polymers also can be used; for instance, those based on acrylics, such as methymethacrylates, as well as porous nylons, porous polyvinyl plastics, and polycarbonates. Additional examples of porous particle bodies are described in U.S. Pat. Nos. 6,613,234, 5,470,463, 5,393,430 and 5,445,732, each of which is incorporated herein by reference.

Ion exchange chromatography separates compounds based on their net charges. Negatively or positively charged functional groups are covalently bound to a solid support matrix, yielding either a cation or anion exchanger, respectively. When a charged compound is applied to an exchanger of opposite charge, it is adsorbed, while compounds that are neutral or the same charge are eluted in the void volume of the column. Binding of the charged compounds is reversible, and adsorbed compounds are commonly eluted with a salt or a pH gradient.

The term "ion exchange resin" refers to a solid, porous network (mineral or organic or composite) carrying ionizable groups of positive or negative sign and of a single group. Positively charged ionic groups (anion exchangers) are, for example, quaternary, tertiary and secondary amines and pyridine derivatives. Negatively charged ionic groups (cation exchangers) are, for example, sulfonates, carboxylates and phosphates.

Selection of an ion exchange resins depends on the properties of the compounds to be separated. For amphoteric compounds, the pI of the compound and its stability at various pH values determine the separation strategy. At a pH above its pI, the compound of interest will be negatively charged, and at a pH below its pI the compound will be positively charged. Thus, if the compound is stable at a pH above its pI, an anion exchange resin is used. Conversely, if the compound is stable at a pH below its pI, a cation exchange resin is used. The operating pH also determines the type of exchanger to use. A strong ion exchange resin maintains capacity over a wide pH range, while a weak one loses capacity when the pH no longer matches the $pK_a$ of its functional group.

Anion exchangers can be classified as either weak or strong. The charge group on a weak anion exchanger is a weak base, which becomes deprotonated and, therefore, loses its charge at high pH. DEAE-cellulose is an example of a weak anion exchanger, where the amino group can be positively charged below pH 9 and gradually loses its charge at higher pH values. A strong anion exchanger, on the other hand, contains a strong base such as a quaternary amine, which remains positively charged throughout the pH range normally used for ion exchange chromatography (pH 2-12).

Cation exchangers also can be classified as either weak or strong. A strong cation exchanger contains a strong acid (such as a sulfopropyl group) that remains charged from pH 1-14; whereas a weak cation exchanger contains a weak acid (such as a carboxymethyl group), which gradually loses its charge as the pH decreases below 4 or 4.5.

In one embodiment of the invention, strong ion exchangers such as quaternary amines or sulfonic acids are used. Weak ion exchangers, such as tertiary amines and carboxylic acids, also can be used, for example, when separating proteins that have pIs between 5 and 8.

Table 4 provides a list of common ion exchangers.

TABLE 4

| Strong Anion | |
|---|---|
| $CH_2N^+(CH_3)_3$ | Triethylaminomethyl |
| $C_2H_4N^+(C_2H_5)_3$ | Triethylaminoethyl |
| $C_2H_4N^+(C_2H5)_2CH_2CH(OH)CH_3$ | Diethyl-2-hydroxypropyl-aminoethyl |
| $R_1R_2R_3R_4N^+$ | Quaternary amine |
| Weak Anion | |
| $C_2H_4N^+H_3$ | Aminoethyl |
| $C_2H_4NH(C_2H_5)_2$ | Diethylaminoethyl |
| $CH_2\,CH_2N(C_2)_5)_2(-CH_2\,CH_2-NH(C_2H_5)_2)$ Or $CH_2\,CH_2NH(C_2H_5)_2$ | DEAE-cellulose |
| Strong Cation | |
| $SO_3^-$ | Sulpho |
| $CH_2SO_3^-$ | Sulphomethyl |
| $C_3H_6SO_3^-$ | Sulphopropyl |
| $CH_3SO_3^-$ | Methylsulfonate |
| Weak Cation | |
| $COO^-$ | Carboxy |
| $CH_2COO^-$ | Carboxymethyl |

Ion exchange resins are well known in the art. Commercially available ion exchangers useful in this invention include, but are not limited to, Q HyperD, S HyperD, Q Sepharose, S Sepharose, Q HyperZ and CM HyperZ. These resins can be mixed with solid buffer beads, for example, to produce the chromatographic materials of this invention.

Chromatographic material can comprise a volume of ion exchanger from 5% to 95% with the remainder being solid buffer.

Chromatographic material useful for separating proteins from mixtures based on their pI can be produced by combining a solid buffer with an ion exchange resin.

In one embodiment, a solid buffer and ion exchange resin, each attached to different solid supports, are combined to form a mixture. Moreover, the mixture may be a bed of mixed particles.

In another embodiment, a chromatographic material comprises a solid buffer and an ion exchange resin attached to a single solid support, such as a membrane or monolith. In another example, an ion exchange resin is combined with a solid buffer on a single particle. In this embodiment, a solid buffer attached to a particle is prepared first, then a polymer with ion exchange properties and large pores is formed on top of the solid buffer.

Proteins passing through chromatographic material of the invention (e.g., through a column or through a series of chambers 102) will have either a net positive charge or a net negative charge or be neutral, depending on whether their pIs are, respectively, below, above or the same as the pH generated by the solid buffer. Proteins whose charge is opposite that of the ion exchange resin at the pH of the environment bind to the ion exchanger, while neutral or same charge proteins remain unbound and pass through the chromatographic material. That is, for example, a protein that is negatively charged at the pH of the solid buffer will bind to the ion exchange resin if this latter is an anion exchanger. Then, captured proteins can be eluted from the chromatographic material. Thus, the chromatographic material of the invention are useful for separating proteins based on pI.

In another embodiment, proteins are separated from mixtures based on their respective pI using a series of chromatographic material. In a multi-staged column (or series of chambers 102) comprised of different chromatographic material, a discontinuous gradient of pH is generated. Proteins in a mixture passing through such a column (or series of chambers 102) will become ionized differently according to their location in the column (or series of chambers 102). When a protein obtains a charge opposite that of the ion exchange resin, it will bind to it. Thus, a mixture traveling through the column (or series of chambers 102) will be depleted of one protein category at a time as it crosses the different sections of the column (or series of chambers 102).

Thus, one of the separation devices shown in FIGS. 1-10 can comprise a series of chromatographic materials that are successively placed in the chambers 102 of the device. The series of chromatographic materials may include a cation exchanger and solid buffers of pH 9, 7 and 5, respectively (from the top to the bottom). A sample of a biological extract is applied first to a container holding the solid buffer of 9. Proteins that have a pI above pH 9 will be positively charged in this environment and, therefore, will bind to the ion exchanger part of the chromatographic material in a first of the chambers 102; in most biological extracts this represents a minority of the protein species. The neutral or negatively charged proteins will not be bound and are eluted from the first chamber 102/510. This eluate is then loaded to a second chamber 102/510 holding the solid buffer of pH 7. At this pH, the proteins having a pI above 7 will be positively charged and will bind to the ion exchanger. The neutral and positively charged proteins are unbound and are eluted from the second chamber 102/510 holding the chromatographic material. Accordingly, this section of chromatographic material has captured proteins having a pI between 7 and 9, with the proteins that have a pI above 9 having already been captured in the first chamber 102/510. Then, this second eluate is loaded to a third chamber 102/510 holding chromatographic material with solid buffer of pH 5. According to a similar mechanism described above, proteins of pI between 5 and 7 will be captured by the cation exchanger, proteins with pI at or below 5 will not be captured and will be found in the eluate. The bound proteins, which define sub-samples, can be eluted thereafter, by conventional means, from the various chambers 102. Accordingly, the proteins have been fractionated in sub-samples having pI above 9, pI between 7 and 9, pI between 5 and 7 and pI below 5. In a similar way, proteins can be fractionated by cation exchange chromatography, using chromatographic materials composed of solid buffers of increasing pH.

In one aspect, the series can comprise two, three, four, five, six, seven, eight, nine, ten, eleven or twelve different chromatographic materials. As described above, the chromatographic materials are arranged in the column or chambers 102 in order of increasing or decreasing pH depending on whether an anion exchanger or a cation exchanger, respectively, is used.

In preparing a solution for loading onto a chromatographic adorbent, electrolytes such as simple salts, for example, sodium chloride or potassium chloride, can be used. As biological molecules can act as electrolytes, however, neat water can be used. Modifiers also can be added to a mixture to prevent proteins from aggregating. Examples of such modifiers include, but are not limited to, glycols and non ionic chaotropic agents, such as urea or non-ionic detergents.

Bound proteins can be desorbed using any chemical component capable of eluting proteins from an ion exchange resin. Most generally, salt solutions are used to desorb proteins; however, a pH change also can be used, as well as displacers.

In another embodiment, there is provided an apparatus comprising a series of containers, wherein a first container in the series comprises a fluid inlet and a last container in the series comprises a fluid outlet, and each container in the series is in fluid communication with a next container in the series, and wherein each container in the series comprises a different chromatographic material and the containers are arranged in increasing or decreasing order according to the pH of the chromatographic materials.

In one such embodiment, the chromatographic materials are contained within cartridge or container segments having inlets and outlets. The segments are stackable with and detachable from each other. The segments each contain a different chromatographic material. They can contain filters or membranes that hold the chromatographic material in place. When attached end-to-end, the segments create a column into which a solution can be poured. After the fluid has passed through all of the segments, the segments can be detached from one another and the captured proteins eluted from each segment. See, for example, WO 03/036304 (Schultz et al.).

Figure 2C:
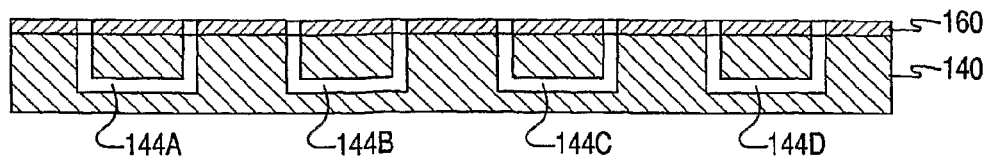
FIG. 2C is a cross-sectional view of a lower conduit plate according to a first embodiment of the present invention.
Figure 3:
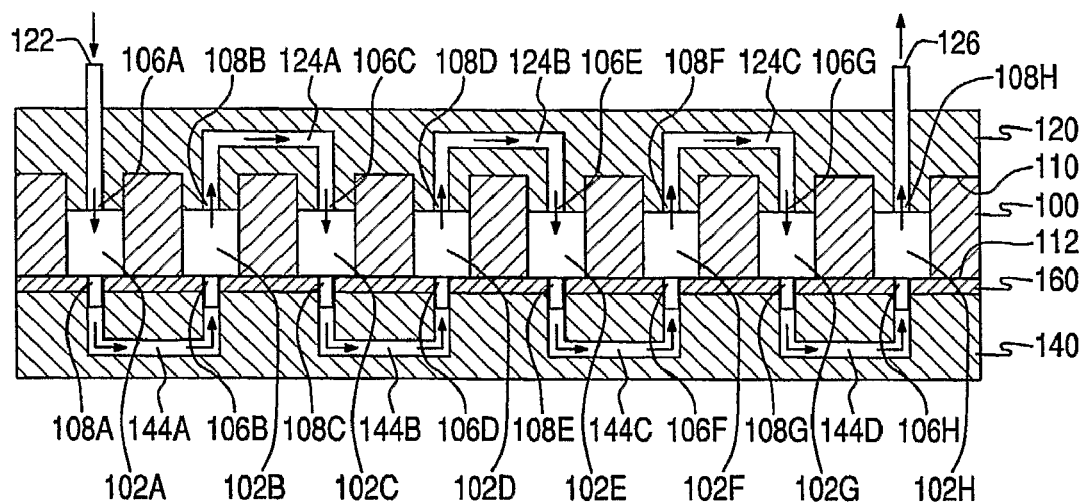
FIG. 3 is an assembled, cross-sectional view of the upper plate, microtiter plate, and lower plate of FIGS. 2A-2C, respectively.

In another such embodiment, the container is a well of a microtiter plate such as that shown in FIGS. 1-3; each container in the series is defined by a chamber 102/510 that is connected by removable conduits. As previously discussed, the plate can be a drip plate or a filter plate. In other embodiments, however, the plate can comprise a piece comprising channels, such as bores, that open on either side of the piece and that will define chambers when conduits are attached to the openings of the bores. Preferably, the chambers 102 are arrayed substantially in a plane.

It is understood that the following examples are for illustrative purposes only and that various modifications or changes in light thereof will be suggested to persons skilled in the art and are to be included within the spirit and purview of this application and scope of the appended claims.

Example 2

Preparation of Solid Buffer of pH 8.5

A solid-phase buffer of pH 8.5 can be prepared by dissolving 10 mMoles of N,N-dimethyl-aminopropyl-acrylamide having a pK of 8.5 (this is 1420 mg of free base) in 50 mL of water. The solution is titrated to pH 8.5 by slow addition of the monomer acrylamidoglycolic acid of pK 3.1 (free acid). Next, 30 g of acrylamide and 2 g of methylene-bis-acrylamide are added to the solution. The volume of the solution is then raised to 100 mL. To this final solution, polymerization catalysts are added, for example ammonium persulfate and TEMED. The solution is then used, for example, to impregnate porous particles. Once the hydrogel has polymerized inside the pores of the particles, the material is washed to remove by-products and reagent excess. The solid-phase buffer can be stored in the presence of 20% ethanol.

Example 3

Preparation of Solid Buffer of pH 4.6

A solid-phase buffer of pH 4.6 can be prepared by dissolving 100 mM of N-acryloyl glycine (pK 4.6) in 1 liter of distilled water. The solution is then titrated to pH 4.6 by adding a concentrated solution (50% in water) of N,N,N-triethyl aminoethyl acrylamide. To the obtained solution, 200 gram of acrylamide and 10 grams of N,N'-methylene-bis-acrylamide are added. The mixture is stirred to complete solubilization. A catalysis system composed of N,N,N',N'-tetramethylethylene diamine and ammonium persulfate is added to the solution just before use. 38 mL of the final solution is added to 100 mL of porous zirconia beads of about 75 µM (pore volume of 38 mL for 100 gram) and mixed to the complete absorption of the solution in the porous volume of the mineral beads. Next, the impregnated beads are degassed under vacuum three times, alternating the introduction of nitrogen. The mixture is then stored at room temperature in the presence of nitrogen until polymerization of the monomers. The resulting solid buffer is washed extensively with water, with a buffer of the same pH (e.g., acetate buffer pH 4.6), and again with water. The solid buffer is then ready for use in the presence of an ion exchanger.

Example 4

Preparation of Solid Buffer of pH 9.3

A solid buffer of pH 9.3 can be prepared by dissolving 100 mM of N,N-dimethyl aminopropyl acrylamide (pK 9.3) in 1 liter of distilled water. The solution is then titrated to pH 9.3 by adding a concentrated solution (50% in water) of acrylic acid. To the obtained solution, 200 gram of dimethyl-acrylamide and 10 grams of N,N'-methylene-bis-acrylamide are added. The resulting mixture is stirred to complete solubilization. A catalysis system composed of N,N,N',N'-tetramethylethylene diamine and ammonium persulfate is added just before use. 38 mL of the final solution is added to 100 mL of porous zirconia beads of about 75 µM (pore volume of 38 mL for 100 gram) and mixed to complete absorption of the solution in the porous volume of the beads. Next, the impregnated beads are degassed under vacuum three times, alternating the introduction of nitrogen. The mixture is then stored at room temperature in the presence of nitrogen until polymerization of monomers. The resulting material is washed extensively with water, a buffer of the same pH (e.g., Tris-HCl buffer, pH 9.3), and again with water. The solid buffer is then ready for use in the presence of an ion exchanger.

Example 5

Preparation of Solid Buffer of pH 7.7

A solid buffer of pH 7.7 can be prepared by dissolving 50 mM of 3-morpholinopropyl acrylamide (pK 7.0) and 50 mM of N,N-dimethylaminoethyl acrylamide (pK 8.5) in 1 liter of distilled water. The solution is then titrated to pH 7.7 by adding a concentrated solution (50% in water) of 2-acrylamido-2-methylpropane sulfonic acid. To the obtained solution, 200 gram of acrylamide and 10 grams of N,N'-methylene-bis-acrylamide are added, and the resulting mixture is stirred to complete solubilization. A catalysis system composed of N,N,N',N'-tetramethylethylene diamine and ammonium persulfate is added just before use. 38 mL of the final solution is added to 100 mL of porous zirconia beads of about 75 µM (pore volume of 38 mL for 100 gram) and mixed to the complete absorption of the solution in the porous volume of the beads. Next, the impregnated beads are degassed under vacuum three times, alternating the introduction of nitrogen. The mixture is then stored at room temperature in the presence of nitrogen until polymerization of monomers. The resulting material is washed extensively with water, a buffer of the same pH (e.g., morpholine-HCl buffer pH 7.7), and again with water. The solid buffer is then ready for use in the presence of an ion exchanger.

Example 6

Preparation of a Mix Mode Chromatographic Material (Solid Buffer of pH 4.6 and Cation Exchanger)

A solid buffer of pH 4.6 can be prepared by dissolving 150 mM of N-acryloyl glycine (pK 4.6) and 10 mM N,N'-methylene-bis-acrylamide in 1 liter of distilled water. The solution is then titrated to pH 4.6 by adding a concentrated solution (50% in water) of N,N,N-triethyl aminoethyl acrylamide. A catalysis system composed of N,N,N',N'-tetramethylethylene diamine and ammonium persulfate is added just before use.

Separately a second aqueous solution composed of 5% of 2-acrylamido-2-methylpropane sulfonic acid sodium salt, 5% of dimethylacrylamide and 1% of and mM N,N'-methylene-bis-acrylamide is prepared. The pH of this solution is then adjusted to 4.6 by addition of a base or an acid. A catalysis system composed of N,N,N',N'-tetramethylethylene diamine and ammonium persulfate is added just before use.

100 mL of porous zirconia beads of about 75 µM (pore volume of 40 mL for 100 gram) are mixed with 20 mL of the first monomer solution and then treated as described in the previous examples up to the polymerization. This intermediate product is washed extensively with water, with a buffer of the same pH (e.g., acetate buffer pH 4.6), and again with water. The washed product is then dried using, e.g., repeated washes with dry ethanol and acetone.

The intermediate dry product is then mixed with 20 mL of the second monomer solution (to fill up the total porous volume of the mineral beads). A second polymerization process is then started as above. The final chromatographic material is washed extensively with water, with acetate buffer pH 4.6, and with distilled water.

Example 7

Preparation of Solid Buffer of pH 6.5

A solid buffer of pH 6.5 can be prepared by dissolving 150 mM of 3-morpholinopropyl acrylamide (pK 7.0) in 1 liter of distilled water. The solution is then titrated to pH 6.5 by adding a concentrated solution (50% in water) of N-acryloyl glycine (pK 3.6). To the obtained solution 400 gram of acrylamide and 30 grams of N,N'-methylene-bis-acrylamide are added, and the resulting mixture is stirred to complete solubilization. A catalysis system composed of N,N,N',N'-tetramethylethylene diamine and ammonium persulfate is added just before use. 100 mL of this solution is dispersed in 500 mL of paraffine oil containing 3% of arlacel C (oil-soluble emulsifier). The suspension is maintained under stirring for 3 hours at 65° C. to allow monomers to copolymerize together. Hydrogel beads formed during polymerization are collected by filtration and washed extensively with a non-polar solvent to eliminate traces of paraffin oil. Next, the beads are washed extensively with water, with a buffer of the same pH, and again with water. The solid buffer is then ready for use in the presence of an ion exchanger.

Example 8

Preparation of Solid Buffer of pH 9.0 Using Irregular Particles

A solid buffer of pH 6.5 can be prepared by dissolving 150 mM of N,N,N-triethyl-aminoethyl-acrylamide (pK 12) in 1 liter of distilled water. The solution is then titrated to pH 9.0 by adding a concentrated solution (50% in water) of acrylamidoglycolic acid (pK 3.1). To the obtained solution, 300 gram of dimethyl-acrylamide and 20 grams of N,N'-methylene-bis-acrylamide are added, and the resulting mixture is stirred to complete solubilization. A catalysis system composed of N,N,N',N'-tetramethylethylene diamine and ammonium persulfate is added just before use. The solution then is placed in a warm bath of 65° C. under nitrogen. Five hours later the polymerization is complete under a full hydrogel block. The hydrogel is cut into small pieces and ground to get particles of about 100 µm. Particulated product is then washed extensively with water, then with a buffer of the same pH, and again with water. The solid buffer is then ready for use in the presence of a ion exchanger.

Example 9

Separation of Proteins Based on pI Using an Anion Exchanger Mixed with Three Different Solid Buffers A series of three chromatographic materials are assembled in a series of interconnected sectional columns or chamber 102/510 (outlet of the previous to the inlet of the following) column or chamber 102/510. Each of the chromatographic materials comprises the same anion exchanger (Q HyperZ sorbent) but a different solid buffer of different pH, in particular, 5.4, 7.7 and 9.5, respectively. The chromatographic sectional columns or chambers 102 are aligned in order of increasing pH, i.e., the first sectional column or chamber 102/510 has a pH of 5.4 and the last adsorbent has pH of 9.5.

The Q anionic sorbent is positively charged in all pH ranges induced by the solid-phase buffers (5.4 to 9.5).

A sample containing five proteins (lysozyme (pI 11), cytochrome c (pI 9.0), myoglobin (pI 7.0), human albumin (pI 6.0) and fetuin (pI≦5.0)) is prepared in 10 mM potassium chloride. To avoid protein-protein interaction, 2M urea is added. The sample is then loaded onto the column or into a first chamber 102/510.

At the first chromatographic material, only fetuin adsorbs because it is the only protein negatively charged at pH 5.4. The remaining four proteins will progress to the second chromatographic material in the column or in a second chamber 102/510.

At the second chromatographic material, both albumin and myoglobin are negatively charged at pH 5.4. Thus, they are captured by the anion exchanger.

At the third chromatographic material in the column or in a third chamber 102/510, only cytochrome C adsorbs because it is the only protein remaining in the sample that is negatively charged at pH 9.5.

Lysozyme possesses a net positive charge at pH 9.5. Accordingly, it will exit the column or the third chamber 102/510 with the flow-through.

Once the adsorption phase is over, the chromatographic materials are disconnected and separately treated to desorb proteins. The bound proteins are desorbed using 1 M potassium chloride, thereby yielding a plurality of sub-samples.

Example 10

Separation of Proteins Based on pI Using a Cation Exchanger Mixed with Three Different Solid Buffers A series of three chromatographic materials are assembled in a series of interconnected sectional columns or chambers 102 (outlet of the previous to the inlet of the following)

column. Each of the chromatographic materials comprises the same cation exchanger but a different solid buffer of different pH, in particular, 5.4, 7.7 and 9.5, respectively. The chromatographic sectional columns or chambers 102 are aligned in order of decreasing pH, i.e., the first sectional column or chamber 102/510 has a pH of 9.5 and the last adsorbent has a pH of 5.4.

The cation exchanger is negatively charged in all pH ranges induced by the solid-phase buffers (5.4 to 9.5).

A sample containing five proteins (lysozyme (pI 11), cytochrome c (pI 9.0), myoglobin (pI 7.0), human albumin (pI 6.0) and fetuin (pI≦5.0)) is prepared in 10 mM potassium chloride. To prevent protein-protein interaction, 2M urea is added. The sample is then loaded onto the column or into a first chamber 102/510.

At the first chromatographic material, only lysozyme adsorbs because it is the only protein negatively charged at pH 9.5. The remaining four proteins progress to the second chromatographic material in the chamber or to a second chamber 102/510.

At the second chromatographic material, only cytochrome C adsorbs because it is the only protein remaining in the sample that is negatively charged at pH 7.7. The remaining proteins progress to the third chromatographic material in the column or to a third chamber 102/510.

At the third chromatographic material, both albumin and myoglobin are negatively charged at pH 5.4. Thus, these proteins are captured by the anion exchanger.

Fetuin possesses a net positive charge at pH 5.4. Thus, fetuin will exit the column or the third chamber 102/510 with the flow-through.

Once the adsorption phase is over, the chromatographic materials are disconnected and separately treated to desorb proteins. The bound proteins are desorbed using 1 M potassium chloride, thereby yielding a plurality of sub-samples.

IV. Fractionation Based on Hydrophobic Index

If there are other methods of separating according to hydrophobic index besides the one we describe here, they should be mentioned.

Another embodiment of the present invention provides methods and systems for reducing the complexity of complex mixtures containing biomolecular components (i.e., chemical species generated by biological processes such as proteins, nucleic acids, lipids, metabolites, etc.) by isolating and detecting biomolecular components, while achieving greater sensitivity and efficiency than heretofore possible.

FIG. 12 provides an illustration of one embodiment of the invention at 1000. A sample solution containing a complex mixture including a plurality of different biomolecular components 1001 is introduced to a sample fractionation column 1002 (or series of chambers 102/510) for at least partial resolution as described hereinbelow. The column 1002 (or series of chambers 102/510) includes a plurality of sorbent materials 1004, 1006, 1008, and 1010 arranged serially (e.g., in successive chambers 102/510) and through which the sample solution 1001 is successively passed, thereby isolating each of the sorbent materials and enabling any remaining solution to be eluted to a receptacle 1012.

In one embodiment of the invention, the sorbent materials are chosen such that substantially all of the biomolecular components are captured by sorbents 1004, 1006, 1008, 1010. In a more particular embodiment of the present invention, each of the sorbents 1004, 1006, 1008, 1010 captures a substantially unique subset of the plurality of biomolecular components. Thus, sorbent 1004 is effective to capture sub-sample 1014, sorbent 1006 is effective to capture sub-sample 1016, sorbent 1008 is effective to capture sub-sample 1018, and sorbent 1010 is effective to capture sub-sample 1020. Following capture of the various sub-samples of the plurality of biomolecular components in the sample solution 1001, the sorbents, including the captured biomolecular components, may be more permanently isolated (i.e., removed from the column or chambers 102/510). The sub-samples may be eluted or otherwise removed from the sorbents for further processing pursuant to a multidimensional separation protocol, as later discussed in greater detail.

The multiplex separation methods of this invention are particularly useful for fractionating analytes in complex mixtures, e.g., samples comprising at least 1000, at least 100,000 or at least 10,000,000 different biomolecular species (e.g., proteins). The methods of this invention are particularly useful for separating biomolecules from biological samples. Such samples can include, for example, amniotic fluid, blood, cerebrospinal fluid, intraarticular fluid, intraocular fluid, lymphatic fluid, milk, perspiration plasma, saliva semen, seminal plasma, serum, sputum, synovial fluid, tears, umbilical cord fluid, urine, biopsy homogenate, cell culture fluid, cell extracts, cell homogenate, conditioned medium, fermentation broth, tissue homogenate and derivatives of these.

An advantage of the present invention is that the device is to use and readily adaptable to any desired number of separations. Moreover, other than some basic lab equipment, including, e.g., a peristaltic pump and/or a vacuum station, no additional equipment may be needed.

In another embodiment, this invention provides a kit. The kit contains a device of this invention and at least one container comprising a separation medium. Such a kit is useful because it enables the user to define the particular arrangement of chambers that will comprise the separation media and what the particular series of separation media will be. Accordingly, in some embodiments, the kit comprises a plurality of different separation media. The kit optionally can comprise at least one container that comprises a fluid, such as a buffer, for use in transporting a sample from one chamber to another during the use of the device.

Example

A separation protocol of human serum using one of the aforementioned embodiments is hereafter set forth.

Step 1: Chambers within a column of a 96-chamber (eight by twelve) microtiter filter plate (Princeton Separations, N.J., USA, long drip nozzles, 25 µM membrane pore size) of the type shown in FIG. 10 were filled with 150 µl (total packed bed volume) of the following functionalize resins: protein-A, blue trisacryl, MEP, heparin, green dye ligand and phenyl-propyl.

Step 2: After connecting (a) the outlet of the first chamber to the inlet of the second chamber, (b) the outlet of the second chamber to inlet of the third chamber (and so on) with plastic tubing, a peristaltic pump (Bio-Rad model EP-1 Econo Pump) was connected to the inlet of the first chamber. Twenty volumes of binding buffer (1×PBS pH 7 [16 volumes], 1M Tris-HCl buffer pH 8 [9 volumes] and deionized water [75 volumes] were then pumped through the chambers (i.e., across the series of resins) at a flow rate of 0.2 ml/min.

Step 3: After equalization with the binding buffer volumes, 40 µl of denatured serum (human serum from Intergen, Norcross, Ga., USA, which was denatured by adding 2 ml serum to 2.5 mL 9M Urea, 2% CHAPS (3-[(cholamidopropyl)dimethylamino]-1-propanesulfonate) for one hour at room temperature) was diluted 1:5 in the binding buffer. The diluted serum was then introduced into the inlet of the first chamber.

Step 4: The flow through the chambers was reestablished at a rate of 0.02 ml/min using the binding buffer. For the first 60 minutes, the effluent from the outlet of the final chamber was discarded.

Step 5: After the first 60 minutes, the effluent was collected for an additional 60 minutes.

Step 6: After a total of 120 minutes, the flow was stopped and all plastic tubing was removed from the microtiter plate.

Step 7: Excess buffer within each of the wells was removed by vacuum and discarded.

Step 8: Captured proteins from each of the wells were then individually eluted using either (i) TFA (0.8 volumes)—water (79.2 volumes)—ACN (6.6 volumes)—IPA (13.4 volumes) or (ii) ammonium hydroxide (8 volumes)—water (72 volumes)—ACN (6.6 volumes)—IPA (13.4 volumes). Specifically, protein elution was performed by incubating the sorbents while gently mixing for 20 minutes.

Step 9: Supernatants from each sorbent were recovered by vacuum filtration into a collection plate, frozen, and lyophilized. Lyophilized residue was then re-dissolved in 100 μL of 25 mM Tris-HCl buffer, pH 7.5 or 150 μl 50 mM Hepes, 0.1% OGP buffer. Aliquots of the re-dissolved lyophilized residue were then analyzed by SELDI-mass spectrometry analysis (Ciphergen Biosystems Inc., Fremont, Calif., USA). Using this method, a total of eight fractions, including flow-through, were obtained from each sample.

Step 10: Each spot of a Q10 ProteinChip array (Ciphergen Biosystems Inc.) was equilibrated two times with 150 μL of the indicated array-specific binding buffer for five minutes as described completely in the manufacturer's instructions. Each spot surface was then loaded with 30 μL (50 μL in case of 150 μL of dissolving buffer) of the sample previously half-diluted in the array binding buffer.

Step 11: After an incubation period of 30 minutes under vigorous shaking, each spot was washed two times with 150 μL of the binding buffer for five minutes to eliminate non-adsorbed proteins. Subsequently, each spot was quickly rinsed with deionized water.

Step 12: All surfaces were dried and loaded twice with 0.5 μL of a saturated solution of SPA in a mixture of ACN (49.5 volumes)-TFA (0.5 volumes)-deionized water (50 volumes), and dried again.

Step 13: All arrays were then analyzed using a mass spectrometer reader used in a positive ion mode, with an ion acceleration potential of 20 kV and a detector voltage of 2.8 kV. The molecular mass range investigated by mass spectrometer m/z was from 0 to 300. Focus mass was set at 30 and 7 for high- and low-mass range, respectively. Laser intensity responsible for the desorption/ionization of proteins on the spot surface was set at 200 and 180 units for high- and low-mass range, respectively, and sensitivity of the detector at 9 units.

Figure 11:
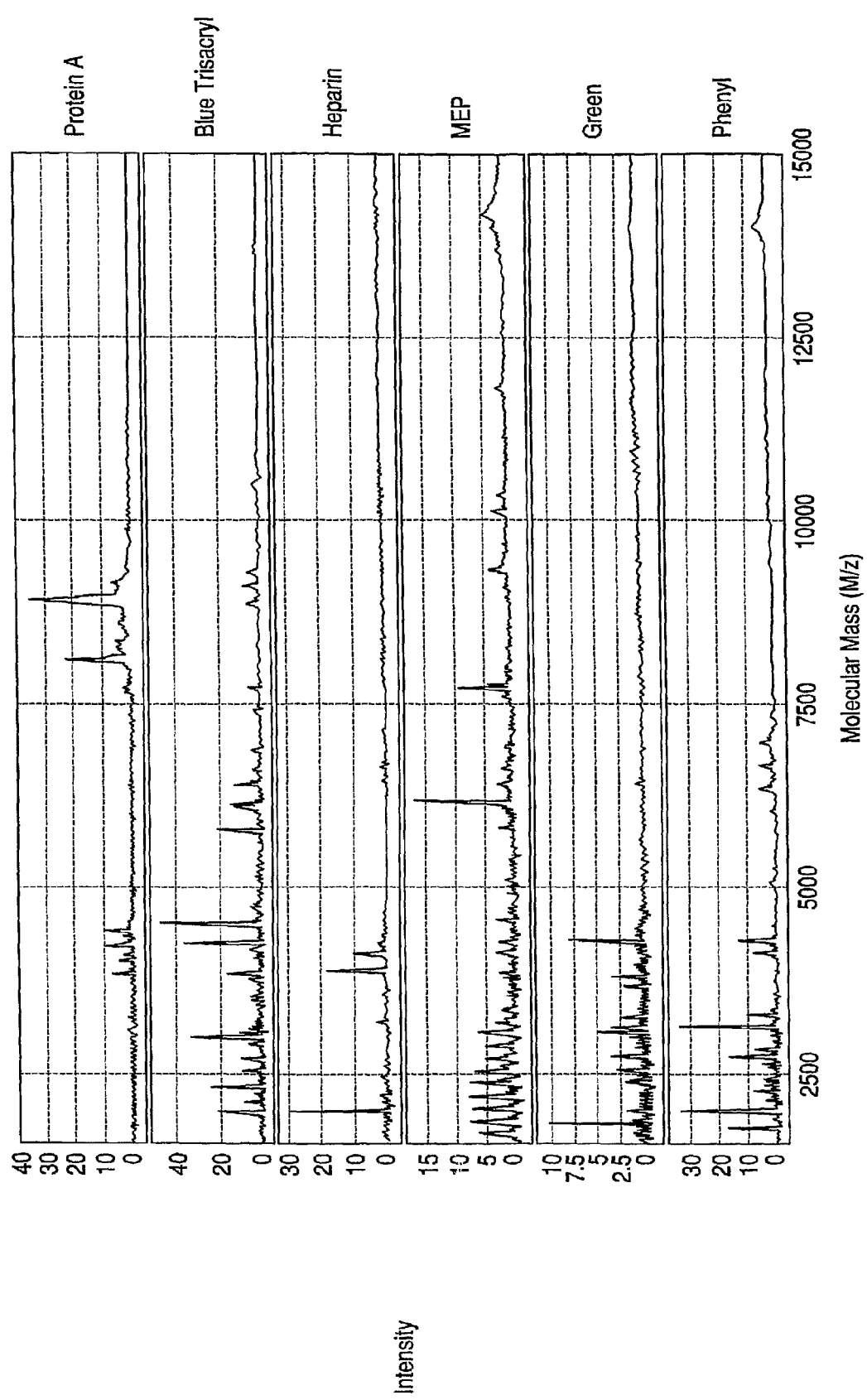
FIG. 11 is a chart of a fractionation of human serum via a series of chromatographic resins.

Step 14: The results of the mass spectrometry are shown in FIG. 11, which charts the fractionation of the human serum.

Although the aforementioned describes embodiments of the invention, the invention is not so restricted. It will be apparent to those skilled in the art that various modifications and variations can be made to the disclosed embodiments of the present invention without departing from the scope or spirit of the invention.

Figure 12A:
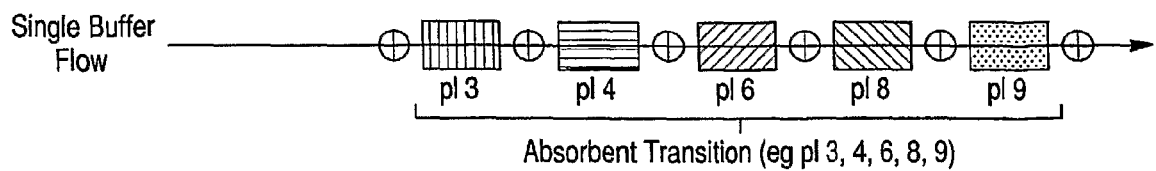
FIGS. 12A-12F show an alternate embodiment multidimensional separation protocol that is conducted in a matrix of chambers that are interconnected via a series of valves.
Figure 12B:
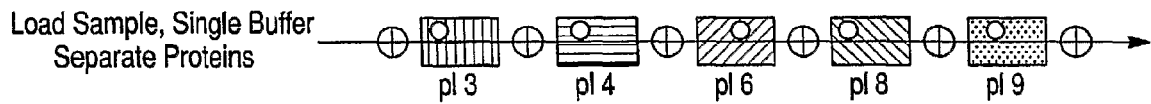
Figure 12C:
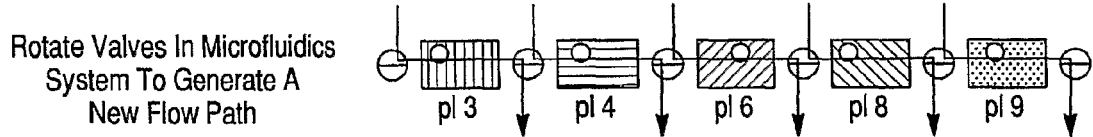
Figure 12D:
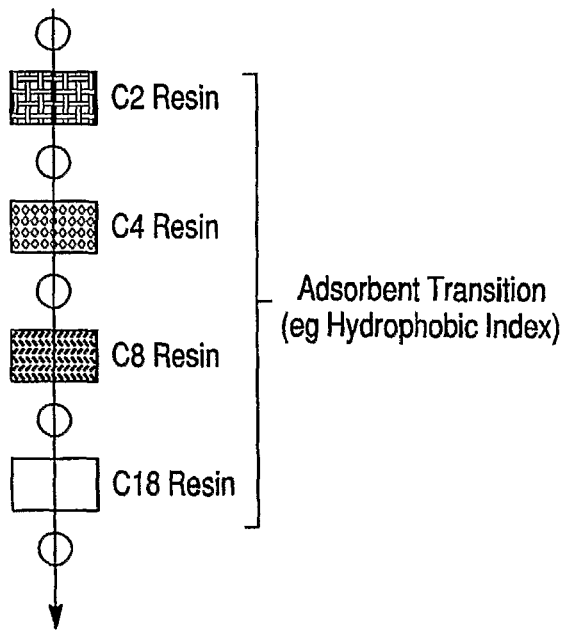
Figure 12E:
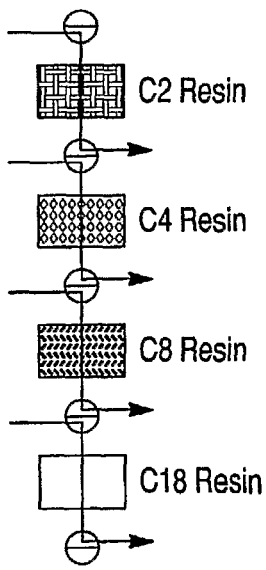
Figure 12F:
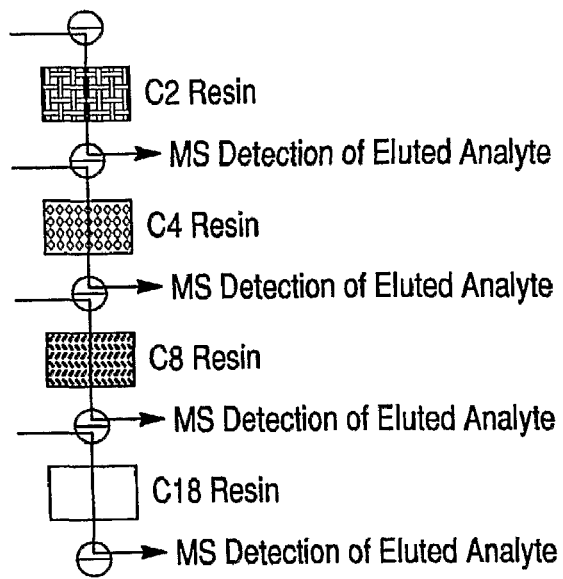

For example, the aforementioned tubes/conduits could be replaced and/or enhanced with a series of valves, as shown in FIGS. 12A-12F. Specifically, each chamber in a standard 96-well plate could be connected to each of the three or four chambers immediate adjacent thereto in the same row and column by conduits in which valves are present, as shown in FIG. 12A. During a first separation protocol (e.g., pI separation) shown in FIG. 12B, the valves connecting each of the chambers along a particular row could be opened whereas all other valves are closed. As a result, a first separation protocol could proceed through the valve-open conduits in the row. Subsequently, each of the valves along the row could be closed followed by an opening of each of the valves in one or more of the columns intersecting the row, as shown in FIG. 12C. Second separation protocols (e.g., hydrophobicity separation) could then proceed through the valve-open conduits in the columns, as shown in FIG. 12D. Further, if the second separation protocol in FIG. 12D proceeded through only one column, each of the valves along that column could be closed followed by an opening of each of the valves in one or more of the other rows intersecting the column, as shown in FIG. 12E. Third separation protocols (e.g., mass spectrometry) could then proceed through the valve-open conduits in those rows, as shown in FIG. 12F.

Accordingly, these other fluidic devices and related separation methods are fully within the scope of the claimed invention. Therefore, it should be understood that the fluid devices and methods described herein are illustrative only and are not limiting upon the scope of the invention, which is indicated by the following claims.

What is claimed is:

1. A device comprising:
   at least three chambers arrayed in a plate, wherein
   (i) the device has a first face on one side of the plate and a second face on a second, opposite side of the plate,
   (ii) each chamber, independent of any other chamber, has an inlet opening to one face and an outlet opening to the other face;
   (iii) a plurality of the chambers are successively connected in series through removable conduits, wherein each conduit connects an outlet of one chamber with an inlet of another chamber; and
   (iv) the series of chambers and conduits defines a fluid path connecting an inlet of a first chamber through each of any intermediate chambers to an outlet of a last chamber, wherein each of the chambers in the series contains a separation medium.

2. The device of claim 1, wherein at least some of the conduits pass through the plate and connect outlets opening to the second face with inlets opening to the first face.

3. The device of claim 2, wherein all of the conduits connect outlets opening to the second face with inlets opening to the first face.

4. The device of claim 2, wherein a plurality of the chambers in the series are arrayed in a linear series, wherein each of the chambers is adjacent to a channel that opens to both faces, and wherein a fluid path between at least one outlet and inlet passes through the channels adjacent to the chambers.

5. The device of claim 1, wherein at least some of the conduits connect outlets opening to the first face with inlets opening to the first face, or outlets opening to the second face with inlets opening to the second face.

6. The device of claim 4, wherein at least one of the conduits connects an outlet opening to the second face with an inlet opening to the second face, and wherein at least one of the conduits connects an outlet opening to the first face with an inlet opening to the first face.

7. The device of claim 1, wherein the conduits are removable from the device.

8. The device of claim 1, wherein a plurality of the chambers in the series contain different separation media.

9. The device of claim 8, wherein the series of separation media comprise, in the direction of the fluid path, either: (a) a high selective medium, a medium selective medium, and a low selective medium; or (b) a low selective medium, a medium selective medium, and a high selective medium.

10. The device of claim 1, wherein the plurality of chambers in the device is a multiple of 8.

11. The device of claim 1, wherein the plurality of chambers in the device is a multiple of 12.

12. The device of claim 1, wherein the chambers are arrayed in at least one linear series.

13. The device of claim 1, wherein the chambers are arrayed in a plurality of rows and columns.

14. The device of claim 13, wherein the chambers are arrayed in an eight-by-twelve array.

15. The device of claim 1, comprising a plurality of series of chambers and conduits defining fluid paths.

16. The device of claim 1, further comprising a collection plate comprising a plurality of wells that are arranged, in rows and columns, to correspond to the chambers of the device, wherein:
   each of the wells of the collection plate has an inlet; and
   upon disengagement of the conduits, the inlets of the wells of the collection plate are configured to align with the chambers of the device.

17. The device of claim 1, further comprising a pump that is configured to push or pull a fluid sample along the fluid path.

18. The device of claim 1, further comprising a drip-through microtiter plate that comprises wells corresponding to the chambers.

19. A device comprising:
   (a) a plate comprising at least one row of chambers, each chamber comprising an inlet on a first face of the plate and an outlet on a second, opposite face of the plate;
   (b) a removable first member that sealingly engages the first face of the plate, wherein the first member comprises:
      (I) a plurality of openings aligned with the inlets of a set of odd-numbered wells, and
      (II) a plurality of open-ended conduits aligned with a set of even-numbered wells, wherein the conduits pass from the inlets to the outlets of the even-numbered wells;
   (c) a removable second member that sealingly engages the first member, wherein the second member comprises:
      (I) an opening aligned with the inlet of a first chamber, thereby forming the inlet to the first chamber; and
      (II) a plurality of conduits, wherein each of the conduits connects an opening of the first member to a conduit of the first member;
   (d) a removable gasket that sealingly engages the second face of the plate, wherein the gasket comprises a plurality of openings aligned with the outlets of the chambers; and
   (e) a removable third member that sealingly engages the gasket, wherein the third member comprises a plurality of grooves aligned with the openings in the gasket that, together, form a plurality of conduits, each conduit connecting the outlet of an odd-numbered well to the outlet of an even-numbered well,
   wherein the combination of chambers and conduits defines a fluid path that passes through odd-numbered wells from inlet-to-outlet and through even-numbered wells from outlet-to-inlet.

20. The device of claim 19, wherein each of the odd-numbered chambers contains a separation medium.

21. A device comprising:
   (a) a plate comprising at least one row of chambers, each chamber comprising a first opening on a first face of the plate and a second opening on a second, opposite face of the plate, wherein the openings define inlets and outlets for each of the chambers;
   (b) a removable first member that sealingly engages the first face of the plate, wherein the first member comprises:
      (I) an inlet port aligned with the first opening, which is configured to serve as inlet, of a first of the chambers in the row, and
      (II) a plurality of conduits that successively connect pairs of the first openings of other chambers in the row;
   (c) a removable gasket that sealingly engages the second face of the plate, wherein the gasket comprises a plurality of openings aligned with the second openings of the chambers; and
   (d) a removable third member that sealingly engages the gasket, wherein the third member comprises a plurality of conduits that successively connect pairs of the second openings of other chambers in the row,
   wherein the combination of openings and conduits defines a fluid path passing from inlet of the chamber to the outlet of the last chamber in the row.

22. The device of claim 21, wherein each of the odd-numbered wells chambers contains a separation medium.

23. A device comprising:
   (a) a plate comprising at least one pair of first and second rows of wells, each well comprising an inlet on a first face of the plate and an outlet on a second, opposite face of the plate;
   (b) a removable first member that sealingly engages the first face of the plate, wherein the first member comprises:
      (I) a plurality of openings aligned with the inlets of wells in a first row, thereby defining chambers, and
      (II) a plurality of open-ended channels aligned with wells in a second row, wherein the channels define conduits passing from the inlets to the outlets of the wells;
   (c) a removable second member that sealingly engages the first member, wherein the second member comprises:
      (I) an opening aligned with an opening in the first member that is aligned with an inlet of a first well in a first row, thereby forming the inlet to the first chamber; and
      (II) a plurality of grooves aligned with the openings of the first member that, together, form a plurality of conduits, each conduit connecting an $n^{th}$ inlet of a well in a first row with an $n^{th}$ inlet of a well in a second row;
   (d) a removable gasket that sealingly engages the second face of the plate, wherein the gasket comprises a plurality of openings aligned with the outlets of the wells; and
   (e) a removable third member that sealingly engages the gasket, wherein the third member comprises:
      (I) a plurality of grooves aligned with the openings in the gasket that, together, form a plurality of conduits, each conduit connecting an $n^{th}$ outlet of a well in a first row with an $n+1^{th}$ outlet of a well in a second row; and
      (II) an opening aligned with an outlet of a last chamber;
   wherein the combination of wells and conduits defines a fluid path passing from inlet to outlet of the wells in a first row.

24. The device of claim 23, wherein:
   (i) the second removable member comprises a first sub-part and a second sub-part, wherein:
      (1) the first sub-part comprises an opening aligned with the opening in the first member, and (2) the second sub-part comprises an opening aligned with the opening in the first member and a plurality of openings that form the grooves when the first sub-part is pressed against the second sub-part; and (ii) the third removable member comprises a third sub-part and a fourth sub-part, wherein:

(1) the third sub-part comprises an opening aligned with the outlet of the last chamber, and (2) the fourth sub-part comprises an opening aligned with the outlet of the last chamber and a plurality of openings that form the grooves when the third sub-part is pressed against the fourth subpart.

25. The device of claim 23, wherein the odd-numbered wells contain a separation medium.

26. A method comprising the steps of:

(a) providing a device comprising:

at least three chambers arrayed in a plate, wherein (i) the device has a first face on one side of the plate and a second face on a second, opposite side of the plate, (ii) each chamber, independent of any other chamber, has an inlet opening to one face and an outlet opening to the other face;

(iii) a plurality of the chambers are successively connected in series through removable conduits, wherein each conduit connects an outlet of one chamber with an inlet of another chamber;

(iv) the series of chambers and conduits defines a fluid path connecting an inlet of a first chamber through each of any intermediate chambers to an outlet of a last chamber; and (v) each chamber in the series comprises a different separation medium;

(b) flowing a sample comprising a plurality of analytes along the fluid path from the inlet of a first chamber through the outlet of the last chamber, whereby the separation media capture analytes having affinity for the media;

(c) removing the conduits that connect outlets to inlets from the device;

(d) eluting captured analytes independently from the chambers; and (e) collecting the eluted analytes.

27. The method of claim 26, further comprising the step of detecting analytes eluted from at least one chamber.

28. The method of claim 26, wherein the step of detecting analytes is performed by mass spectrometry or gel electrophoresis.

29. The method of claim 26, wherein the step of eluting comprises eluting from at least one chamber in a plurality of fractions.

30. The method of claim 26, wherein the sample is selected from the group consisting of blood, urine, cerebrospinal fluid and derivatives thereof.

31. The method of claim 26, further comprising the step of (b)(1) separating at least one of the analytes captured by the separation media into two or more mini-samples.

32. The method of claim 26, further comprising the step of (b)(1) separating at least one of the analytes captured by the separation media into two or more mini-samples using one or more of the following protocols: mass spectrometry, isoelectric focusing, hydrophobicity, and/or hydrophilicity.

33. A device comprising:

a plurality of intersecting row and columns arranged in a plate, wherein each of the rows comprises a plurality of sample chambers that are configured to be fluidically connected to the other chambers in the row, wherein each of the columns comprises a plurality of sample chambers that are configured to be fluidically connected to the other chambers in the row, wherein at least some of the chambers in one of the rows comprise chromatographic separation media that are configured to capture molecules that have pI values within a given range and wherein the chromatographic separation media of the chambers are sequentially arranged from lowest-to-highest or highest-to-lowest in the chambers in the row, wherein at least some of the chambers in at least one of the columns comprise hydrophobic separation media that are configured to capture molecules that have hydrophobicity values within a given range and wherein the hydrophobic separation media of the chambers are sequentially arranged from lowest-to-highest or highest-to-lowest in the chambers in the column.

34. A method for the multidimensional separation of analytes comprising:

(a) providing a device comprising a plurality of intersecting row and columns arranged in a plate, wherein each of the rows comprises a plurality of sample chambers that are configured to be fluidically connected to the other chambers in the row, wherein each of the columns comprises a plurality of sample chambers that are configured to be fluidically connected to the other chambers in the row, wherein at least some of the chambers in one of the rows comprise chromatographic separation media that are configured to capture molecules that have pI values within a given range and wherein the chromatographic separation media of the chambers are sequentially arranged from lowest-to-highest or highest-to-lowest in the chambers in the row, wherein at least some of the chambers in at least one of the columns comprise hydrophobic separation media that are configured to capture molecules that have hydrophobicity values within a given range and wherein the hydrophobic separation media of the chambers are sequentially arranged from lowest-to-highest or highest-to-lowest in the chambers in the column;

(b) providing a sample to a first chamber in the row that comprises the chambers that contain the chromatographic separation media;

(c) separating the sample into a plurality of sub-samples respectively provided in each of the chambers of the row by passing the sample through the series of chromatographic separation media in the row; and (d) separating the subsample in at least one of the chambers of the row into a plurality of mini-samples respectively provided in each of the chambers of the intersecting column by passing the sample through the series of hydrophobic separation media in the column.

* * * * *